United States Patent [19]
Hata

[11] Patent Number: 5,585,559
[45] Date of Patent: Dec. 17, 1996

[54] ENVIRONMENT MEASURING APPARATUS

[75] Inventor: Shigeo Hata, Yokohama, Japan

[73] Assignee: Canon Kabushiki Kaisha, Tokyo, Japan

[21] Appl. No.: 409,056

[22] Filed: Mar. 25, 1995

[30] Foreign Application Priority Data

Mar. 25, 1994 [JP] Japan .................. 6-056044

[51] Int. Cl.⁶ .................................. G01N 27/00
[52] U.S. Cl. .................... 73/335.02; 73/335.05
[58] Field of Search ................. 73/335.05, 335.02

[56] References Cited

U.S. PATENT DOCUMENTS

| 3,523,244 | 8/1970 | Goodman et al. | 73/335.05 |
| 4,386,336 | 5/1983 | Kinomoto et al. | 73/335.05 |
| 4,419,021 | 12/1983 | Terada et al. | 73/335.05 |

FOREIGN PATENT DOCUMENTS

| 88144 | 4/1989 | Japan | 73/335.02 |
| 210858 | 8/1989 | Japan | 73/335.02 |

Primary Examiner—Hezron E. Williams
Assistant Examiner—Daniel S. Larkin
Attorney, Agent, or Firm—Fitzpatrick, Cella, Harper & Scinto

[57] ABSTRACT

A humidity measuring apparatus includes a device having a resistance thereof varied with a change of humidity, a resistor connected to the device, an oscillation circuit for supplying a square wave of a predetermined frequency across the device and the resistor, and a measuring unit for detecting a voltage between the device and the resistor to measure humidity. The oscillation circuit selectively supplies a square wave of a first frequency and a square wave of a second frequency lower than the first frequency. Thus, the humidity is measured with a high precision.

8 Claims, 21 Drawing Sheets

PULSE WAVEFORM APPLIED TO HUMIDITY SENSOR IN FIG. 7

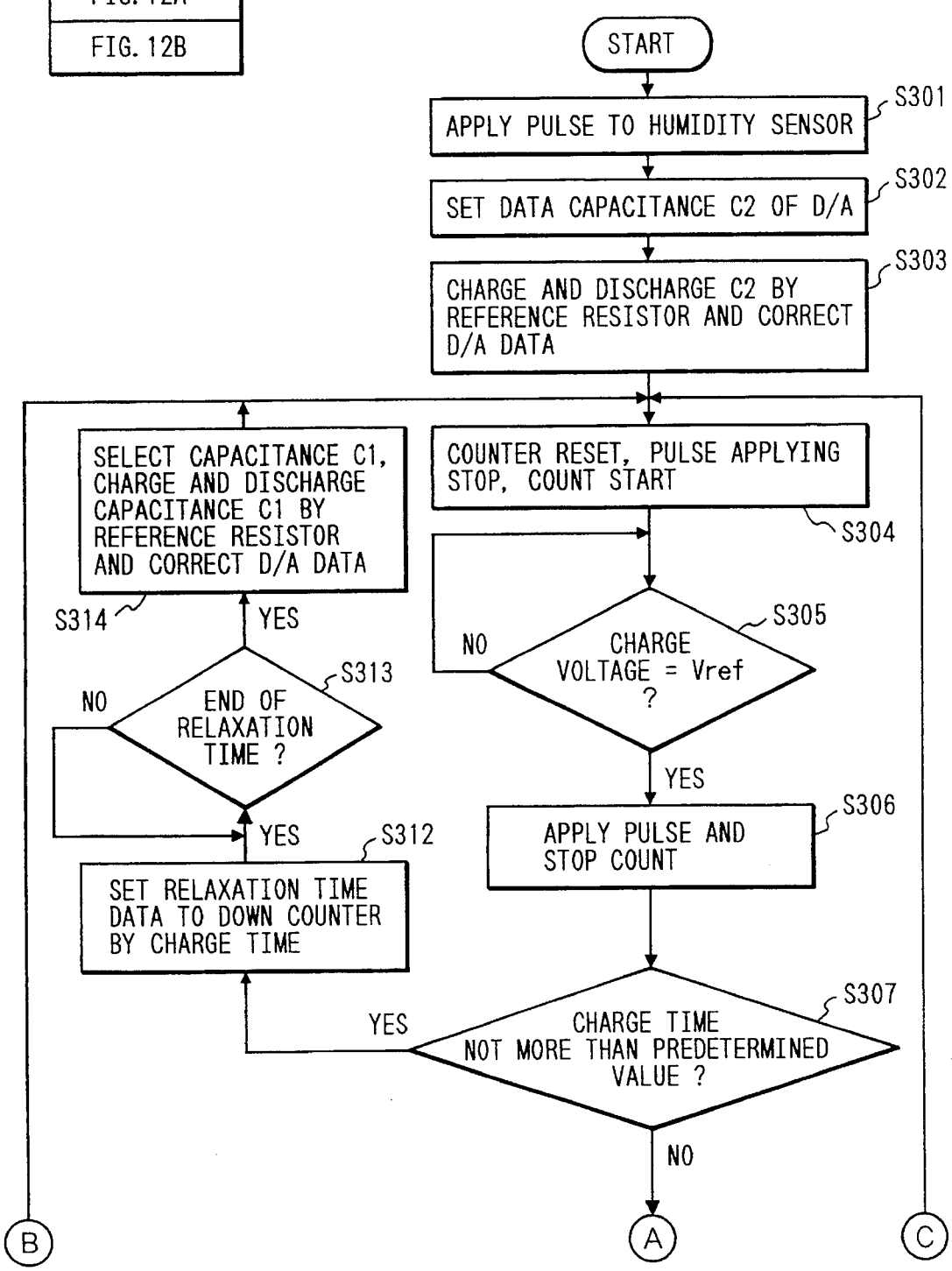

ENVIRONMENT MEASURING APPARATUS

BACKGROUND OF THE INVENTION

1. Field of the Invention

The present invention relates to an environment measuring apparatus which uses an element having a resistance thereof changed with a change of environment.

2. Related Background Art

FIG. 18 shows a circuit configuration of a prior art environment measurement apparatus for detecting an environment condition such as a temperature or a humidity. In FIG. 18, numeral 101 denotes a current generation circuit for supplying power (+9 V, −9 V) to respective units, numeral 102 denotes a sensor unit having a thermistor 103 as a temperature sensor and a humidity sensor 104, numerals 105, 106, and 109 denote operational amplifiers, numeral 107 denotes a rectifying detection circuit, numeral 108 denotes a filtering integration circuit, numeral 110 denotes an oscillation circuit for applying a pulse of predetermined frequency and amplitude to the humidity sensor 104 through a resistor (R11) 116, and numeral 113 denotes environment condition detection means including the operational amplifiers 106 and 109, the detection circuit 107 and the integration circuit 108. Numerals 114 and 115 denote capacitors having capacitance of C11 and C12.

In the above measurement apparatus, a floating power supply is supplied to terminals P1 and P2 of the power generation circuit 101 to generate ±9 V power which is supplied to the respective units in the apparatus. An oscillation output having the predetermined frequency (e.g., 1 kHz) and amplitude (e.g., 3 V pp) is supplied to the humidity sensor 104 from the oscillation circuit 110 through the resistor 116 and the capacitor 114 having the capacitance C11, and the sensor output is applied to the operational amplifier 106 having a high impedance through the capacitor 115 having the capacitance C12 and is amplified thereby, and the output of the operational amplifier 106 is rectified by the detection circuit 107 and filtered by the integration circuit 108, and the output impedance is lowered by the operation amplifier 109 and a DC output signal is produced from the terminal P4. Thus, when the resistance of the humidity sensor 104 is changed by the environment, its corresponding DC output signal is produced.

FIG. 19 shows another prior art example. Numerals 1–11, 61, 70 and 71 denote analog switches for applying a square wave signal to a humidity sensor 23, connecting the humidity sensor 23 to a reference supply 22 and connecting capacitors 12, 68, and 69 to the humidity sensor 23. Numerals 13–16 denote 2-input AND gates which are used to control a switching timing of the analog switches 6, 8, 9, and 11. Numerals 21 and 22 denote reference supplies of a fixed voltage.

Numeral 55 denotes a D/A converter for producing a comparison reference voltage of a comparator 17 used to measure a resistance of the humidity sensor 23. When a control signal is sent to a signal line 45 by control means 20, digital data is switched.

Numeral 19 denotes count means and the count thereof is used to calculate a humidity by operation means. Numerals 26, 27 and 28 denote inverter circuits which invert the inputs thereto to produce inverted outputs. The above components are connected as described below.

One end of each of the capacitors 12, 68 and 69 having the other end thereof grounded is connected to one end of the analog switch 1, 2, or 70, and the other end of the analog switch 1, 2, or 70 is connected to a signal line 31 through which a positive signal input terminal of the comparator 17, a signal input terminal of the analog switch 3 having the other end thereof grounded and one of signal input terminals of the analog switch 7 are connected. An analog signal output terminal of the D/A converter 55 is connected to a negative signal input terminal of the comparator 17 through a signal line 40.

One signal input terminal of the analog switch 8 having the other signal input terminal thereof grounded is connected to one input signal terminal of each of the analog switches 6 and 7 and one terminal of the humidity sensor 23, and one input terminal of the analog switch 11 having the other input signal terminal thereof grounded is connected to one signal input terminal of each of the analog switches 9 and 10 and the other terminal of the humidity sensor 23. The other signal input terminals of the analog switches 6 and 9 are connected to a positive terminal of a power supply 21 having a negative terminal thereof grounded through a common line 48, and the other signal input terminal of the analog switch 10 is connected to a positive terminal of a power supply 22 having a negative terminal thereof grounded through a signal line 46.

Control terminals of the analog switches 1, 2, and 70 are connected to a control signal output terminal of control means 20 through signal lines 37. Control terminals of the analog switches 7 and 10 are connected to an output terminal of the inverter 28 through a signal line 33.

Control terminals of the analog switches 6, 8, 9 and 11 are connected to output terminals of the 2-input AND gates 13–16, respectively, and one input terminal of each of the AND gates 13–16 is connected to a control signal output terminal of the control means 20 through a signal line 32. Other signal input terminals of the AND gates 13 and 14 are connected to a control signal output terminal of the control means 20 through a signal line 54. Similarly, other signal input terminals of the AND gates 15 and 16 are connected to the control signal output terminal of the control means 20 through a signal line 54'. The signal line 32 is connected to one input terminal of the 2-input AND gate 64 and an input terminal of the inverter 26. The three inverters 26, 27, and 28 form a delay inverter, and a signal output terminal of the inverter 26 is connected to a signal input terminal of the inverter 27, and a signal output terminal of the inverter 27 is connected to a signal input terminal of the inverter 28. A signal output terminal of the comparator 17 is connected to a signal input terminal of the count means 19 through a signal line 41.

The control means 20 and the count means 19 are connected by a bilateral signal line 44. The count means 19 outputs operation information to the operation means 18 through a signal line 43. The operation means 18 is connected to the control signal output terminal of the control means 20 through a signal line 42. A signal line 62 is connected to one signal input terminal of the 2-input AND gate 64, and the output terminal of the AND gate 64 is connected to a control terminal of the analog switch 3.

Referring to a flow chart of FIG. 20, an operation is explained.

During non-measurement of humidity, the control means 20 outputs square waves of duty factor of 50% of opposite phases to the signal lines 54 and 54' and outputs a signal "H" to the signal line 32 to enable the AND gates 13–16, and outputs a signal "H" to the signal line 62 to turn on the analog switch 3 to fix the potential of the signal line 31 to the GND potential. The signal line 60 is rendered to "L".

When "H" is outputted to the signal line 54 and "L" is outputted to the signal line 54', the analog switches 6 and 11 are turned on and the analog switches 8 and 9 are turned off. Similarly, when "L" is outputted to the signal line 54 and "H" is outputted to the signal line 54', the analog switches 6 and 11 are turned off and the analog switches 8 and 9 are turned on. Since the signal line 33 is also "L", the analog switches 7 and 10 are turned off. Under this condition, a pulse (square wave) having a duty factor of 50% and a predetermined frequency and an amplitude which is two times as large as the voltage of the power supply 21 shown in FIG. 6 is applied to the humidity sensor 23 (S701).

A procedure for measuring the humidity is now explained.

During the non-measurement state of humidity, the control means 20 sets standard comparison reference digital data at a digital input terminal of the D/A converter 55. A signal is outputted to the signal line 37 to turn on the analog switch 1 and turn off the analog switches 2 and 7 to connect the capacitor 68 of the capacitance C2 which is optimum to measure a middle humidity range to the signal line 31 (S702).

The capacitance C2 of the capacitor 68 is set to a capacitance which fits the intended operation, for example, 6800 pF. The capacitance C1 of the capacitor 12 is set to a capacitance which fits to the measurement of a high humidity range, for example, 0.68 µF, and the capacitance C3 of the capacitor 69 is set to a capacitance which fits to the measurement of a low humidity range, for example, 33 pF. The resistances of the resistors 29, 30, and 72 are set to 1 KΩ, 100 KΩ, and 10 MΩ, respectively, with a precision of no greater than ±1%, to form time constants with C1, C2 and C3.

Under this condition, the control means 20 sends the "H" signal to the signal lines 32, 60 and 62 and turns on the analog switch 5. Then, it sends the "L" signal to the signal line 62 to serially connect the resistor 30 and the capacitor C2. Thus, the reference supply 22 starts to charge the capacitance C2 through the resistor 30. At this time, the control means 20 outputs the "H" signal to the signal line 44 before it outputs the "L" signal to the signal line 32 to previously reset the count means 19.

At the moment when the signal line 62 is rendered "L", the count means 19 detects the "L" level on the signal line 32 and starts the counting. (The count means 19 includes a time base). When the potential of the signal line 31 reaches the comparison reference potential corresponding to the analog output by the comparison reference digital data of the D/A converter 55, the output of the comparator 17 changes from "L" to "H", and when the count means 19 detects the inversion timing, it stops the counting and outputs the count to the signal line 43. The operation means 18 corrects the reference potential applied by the D/A converter 55 to the negative terminal of the comparator 17 relative to a theoretical value of a charge time determined by the capacitance of the charging capacitor and the resistance of the resistor used, and outputs a signal to the control means 20 to change the output data of the D/A converter 55 (S703).

Then, the signal line 62 is rendered from "L" to "H" and the signal line 32 is rendered to "L" so that all of the AND gates 13–16 are disabled producing the output "L". All of the analog switches 6, 8, 9, and 11 are turned off. The analog switch 3 is turned off and the signal line 31 floats.

At the next timing, the signal line 33 is rendered to "H" through the inverters 26–28 and the analog switches 7 and 10 are turned on so that the reference supply starts the charging of the capacitance C2 through the humidity sensor 23.

The control means 20 outputs "H" to the signal line 44 immediately before it outputs "L" to the signal line 32 to previously reset the count means 19 as described above.

At the moment when the signal line 32 is rendered to "L", the count means 19 detects the "L" level of the signal line 32 to start the counting (S704). When the potential of the signal line 31 reaches the comparison reference potential corresponding to the analog output by the comparision reference digital data of the D/A converter 55 (S705), the output of the comparator 17 changes from "L" to "H", and when the count means 19 detects the inversion timing, it stops the counting (S706) and outputs the count to the signal line 43. The operation means 18 reads the capacitance of the charging capacitor used, the comparison reference potential of the comparator 17 and the previously measured measurement environment temperature by the control means 20 through the signal line 43 and operates the data on the signal line 43 under the following condition or determines a relative humidity and an absolute temperature by the compare-inversion means by a chart. The above environment measurement is repeated by a predetermined number of times to determine average values of the relative humidities and the absolute temperatures.

When the count of the count means 19 does not reach the predetermined level, the control means 20 receives the information from the signal line 20 and temporarily returns to the humidity measurement mode and starts the measurement of humidity again after a predetermined relaxation time.

At that time, the analog switch 2 is turned on to connect the capacitance C1 to the signal line 31, and the above humidity measurement is repeated (S707, S712 and S713).

When the count of the count means 19 is above the predetermined level, the control means 20 receives the information through the signal line 44 and temporarily returns to the humidity non-measurement mode and measures the humidity again after a predetermined relaxation time.

At this time, the analog switch 70 is turned on to connect the capacitance C3 to the signal line 31 and the above humidity measurement is repeated. Before the capacitance is changed for remeasurement, the data of the D/A converter 55 which applies the reference potential to the negative input terminal of the comparator 17 is compensated in the above compensation method (S708, S714, and S715).

The resistance of the humidity sensor 23 is given by:

$$R = t/(C \times \ln(1/(1 - Vref/Va)))$$

where

R: resistance of the humidity sensor 23

C: capacitance of the capacitors 12, 68 and 69

Vref: reference voltage of the D/A converter 55

Va: reference voltage of the reference supply 22 t: charge time to C from 0 V to Vref

The operation means 18 has a conversion map of the value of t of the resistance R and the relative humdity and determines the resistance by the comparator means (S709–S711).

FIG. 21 shows a circuit configuration of another prior art example. In the present circuit, the resistors 29, 30, and 72 and the analog switches 4, 5 and 71 connected thereto in the circuit of FIG. 19 are omitted. This circuit can similarly measure the environment humidity.

However, in the prior art environment measurement apparatuses described above, a dynamic range of the output is not attained in a low humidity range (the environment range in which the resistance of the humidity sensor is several hundreds MΩ) by the affect of a stray capacity, particularly a wiring capacity connected to the humidity sensor, and as a result, it is difficult to expand a measurable range.

Further, since a stray capacity of approximately 10 pF is inherently attached to the input terminal of the analog switch, if ten or more analog switches are connected to the capacitance under an environment condition in which the resistance of the humidity sensor reaches several GΩ, the measurable range is narrowed because the capacitance increases.

In addition, in the prior art, since the performance of the humidity sensor is deteriorated when an excessive DC voltage is applied thereto, a predetermined non-measurement time to relieve the deterioration of the humidity sensor is set for each measurement and then the humidity measurement is resumed. It has been found by an experiment of the present inventors that if the previous measurement time is 100 ms or longer, for example, by the high resistance of the humidity sensor, the humidity sensor does not recover its initial performance unless the relaxation time is 10 seconds or longer. As the number of times of environment measurement increases, the humidity sensor is deteriorated more and the maintenance of the performance of the apparatus over an extended period is difficult to attain.

In an environment condition (high humidity range) in which the resistance of the humidity sensor decreases, the potential of the positive signal input terminal of the comparator slightly rises by the resistor division by the on-resistance of the analog switch connected to the charging capacitor and the resistance of the humidity sensor immediately after the start of the measurement so that the charging time of the capacitance measured by the count means is shorter than a theoretical time. As a result, the output of the apparatus represents the relative humidity which is higher than the actual relative humidity and a high precision is not attained.

SUMMARY OF THE INVENTION

It is an object of the present invention to provide an environment measuring apparatus which solves the above problems.

It is another object of the present invention to provide an environment measuring apparatus which has a wide environment measurable range, is of low cost, high performance, and high precision.

Other objects and features of the present invention will be apparent from the following description of the specification and the accompanying drawings.

DETAILED DESCRIPTION OF THE PREFERRED EMBODIMENTS

Figure 1:
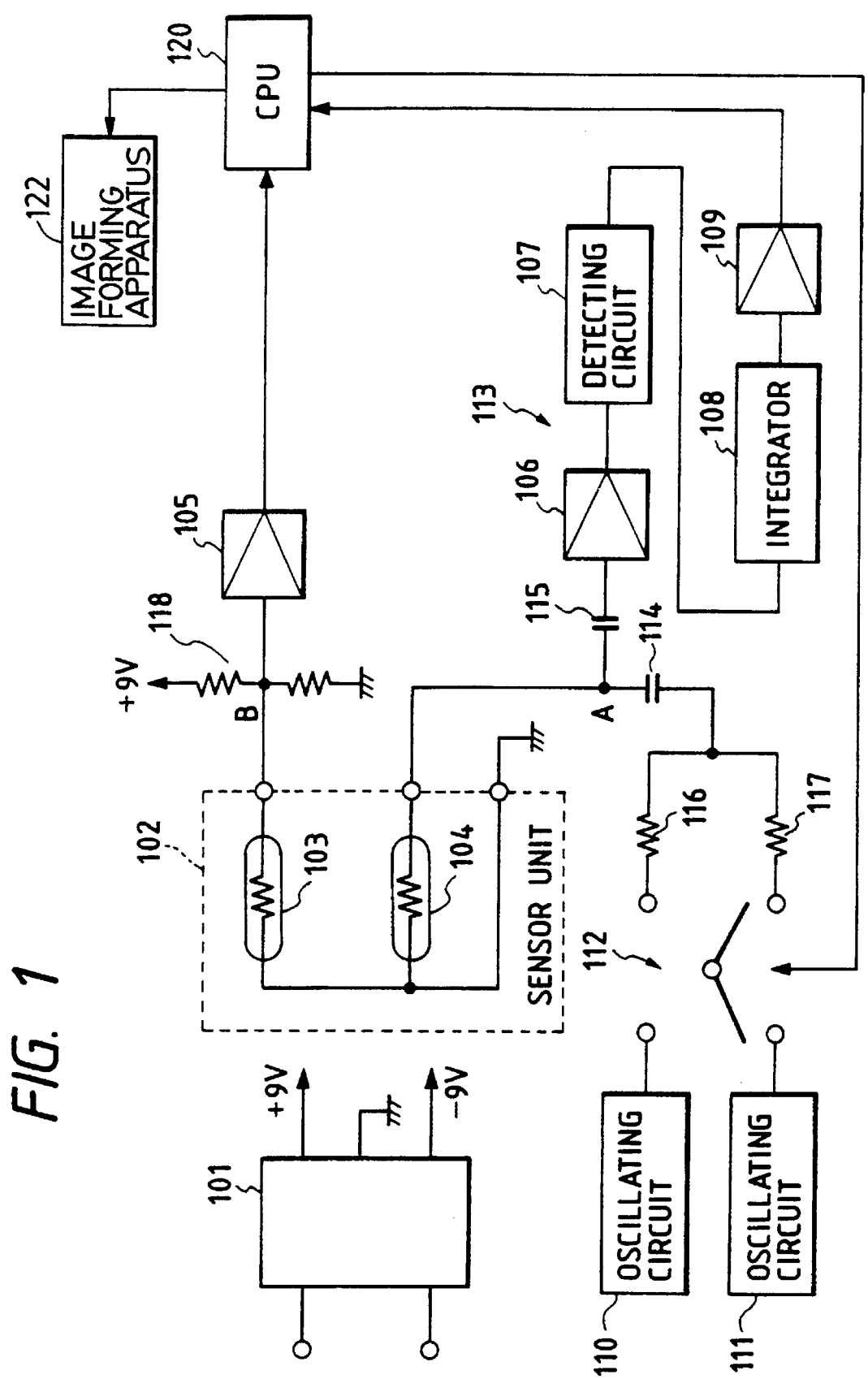
FIG. 1 shows a circuit configuration of a first embodiment of the present invention.

FIG. 1 shows a circuit configuration of a first embodiment of the environment measuring apparatus of the present invention. A power supply circuit 101 supplies a voltage of +9 V or –9 V to the environment measuring apparatus. A sensor unit 102 comprises a thermistor 103 which is a device having a resistance thereof changed with a temperature and a humidity sensor 104 which is a device having a resistance thereof changed with a humidity. The +9 V is applied to the thermistor 103 through a resistor 118 and a voltage at a point B between the thermistor 103 and the resistor 118 is amplified by an operational amplifier 105 which supplies an output to a CPU 120 having an A/D converter built therein. The CPU 120 measures the resistance of the thermistor 103 based on the signal from the operational amplifier 105 to detect a temperature surrounding the thermistor 103.

Figure 2A:
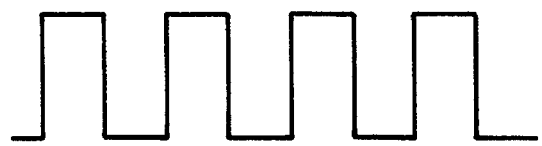
FIGS. 2A–2E show waveforms of the circuit of FIG. 1, FIGS. 3A–3D show waveforms of the circuit of FIG. 1.
Figure 2B:
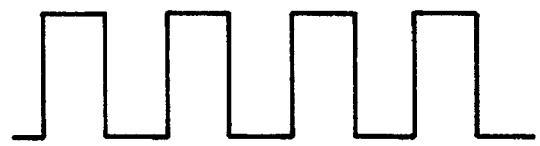
Figure 2C:
Figure 2D:
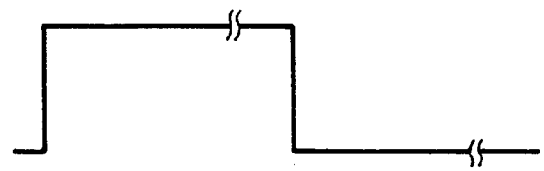

A voltage of 3 V is applied to the humidity sensor 104 from an oscillation circuit 110 or an oscillation circuit 111 through a resistor 116 or a resistor 117 and a capacitor 114. A switch 112 selects one of the oscillation circuits 110 and 111 and one of the resistors 116 and 117. The switch 112 is controlled by the CPU 120. The oscillation circuit 110 applies the voltage of a rectangular wave having an amplitude of 0–3 V and a frequency of 1 KHz as shown in FIG. 2A, and the oscillation circuit 111 applies the voltage of a rectangular wave having an amplitude of 0–3 V and a frequency of 100 Hz as shown in FIG. 2D. The square wave is applied to the humidity sensor 104 because the humidity sensor 104 would be broken if a DC voltage is applied to the humidity sensor 104 for a long time. The resistor 116 is several hundreds KΩ and the resistor 117 is several tens MΩ.

Figure 3A:
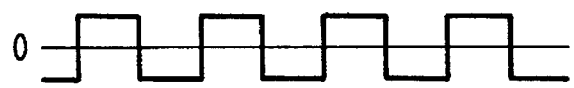
Figure 3B:
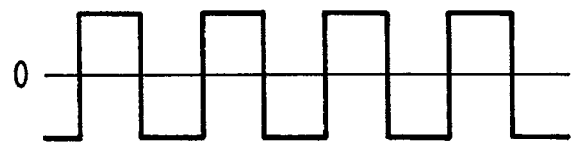
Figure 3C:
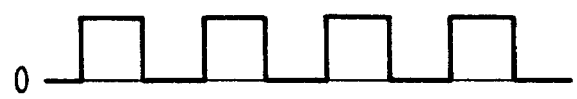
Figure 3D:
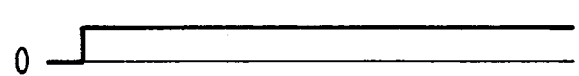

A voltage at a point A between the humidity sensor 104 and the resistor 116 or 117 is inputted to the operational amplifier 106 through a capacitor 115. A voltage waveform between the capacitor 115 and the operational amplifier 106 is a square wave centered at 0 V as shown in FIG. 3A. This waveform is amplified by the operational amplifier 106 as shown in FIG. 3B. The waveform is rectified by a detection circuit 107 as shown in FIG. 3C. The rectified waveform is inputted to an integration circuit 108 which outputs an integration signal as shown in FIG. 3D. The signal is amplified by an operational amplifier 109 and applied to the CPU 120. The CPU 120 measures the resistance of the humidity sensor 104 based on the signal from he operational amplifier 109 to detect the humidity surrounding the humidity sensor 104. The CPU 120 controls respective units of an image forming apparatus 122 based on the detected temperature and humidity.

Figure 4:
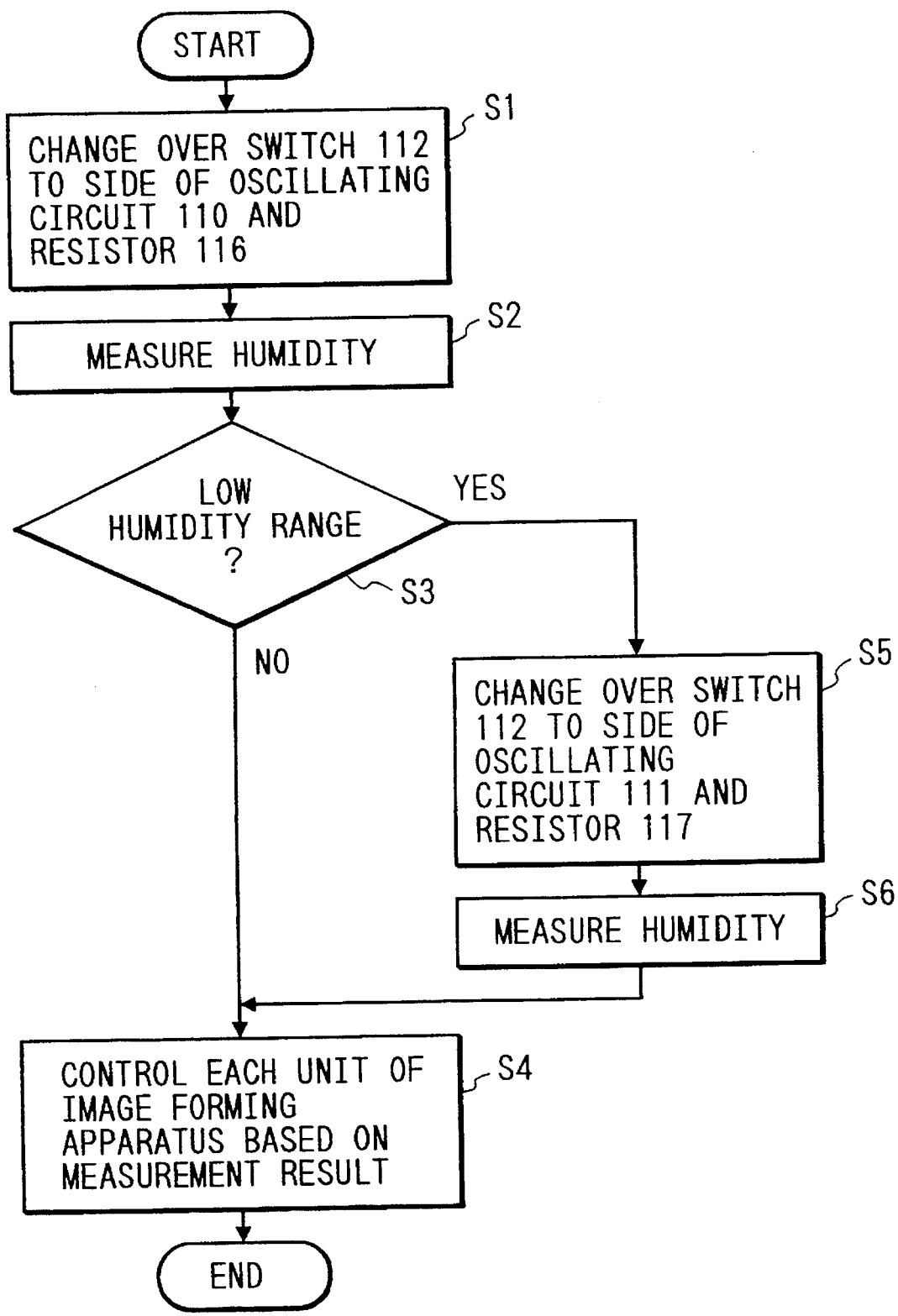
FIG. 4 shows a control flow chart of a CPU 120 of FIG. 1.

FIG. 4 shows a control flow chart for the humidity measurement by the CPU 120. First, the switch 112 is switched to the oscillation circuit 110 and the resistor 116 (step S1), and the humidity is measured based on the signal from the operational amplifier 109 (step S2). Whether the resistance of the humidity sensor 104 is several KΩ—several MΩ (middle/high humidity range) or several tens MΩ—several hundreds MΩ (low humidity range) is determined. If the voltage at the point A in the step S2 is very high, it indicates the low humidity range (step S3). If the middle/high range is detected in the step S3, the units of the image forming apparatus are controlled based on the result of measurement in the step S2 (step S4). If the low humidity range is detected in the step S2, the switch 112 is switched to the oscillation circuit 111 and the resistor 117 (step S5), and the humidity is measured based on the signal from the operational amplifier 109 (step S6). The process then proceeds to the step S4 to control the units of the image forming apparatus based on the result of measurement in the step S6.

Figure 2E:

For the low humidity range, the oscillation circuit 111 having the lower frequency than the oscillation circuit 110 for the middle/high range is selected, and the resistance 117 having the lower resistance than the resistor 116 for the middle/high humidity range is selected. The reason for such selection for the oscillation circuit is described below. In the middle/high humidity range, the voltage waveform at the point A is that shown in FIG. 2B while in the low humidity range the resistance of the humidity sensor 104 is several tens MΩ—several hundreds MΩ and it is susceptible of the effects of a stray capacity of a wiring capacitance on a circuit board. Thus, the voltage waveform at the point A is that as shown in FIG. 2C. From the comparison of FIG. 2B and FIG. 2C, it is seen that in FIG. 2C, the applied voltage from the oscillation circuit reaches 0 V before the voltage at the point A reaches the intended divided voltage so that accurate measurement is not attained by integrating such a voltage. Thus, by applying the voltage of the waveform as shown in FIG. 2D, the voltage waveform at the point A can reach the intended divided voltage so that the accurate measurement is attained as shown in FIG. 2E. The reason for selecting the resistor as described above is that when the resistance of the humidity sensor 104 is several KΩ to several MΩ (middle/high range), the divided voltage by the resistor of several hundreds KΩ is measured and when it is several tens MΩ several hundreds MΩ, the divided voltage by the resistor of several tens MΩ is measured so that the accurate measurement is attained in accordance with the resistance characteristic of the humidity sensor 104.

Figure 5:
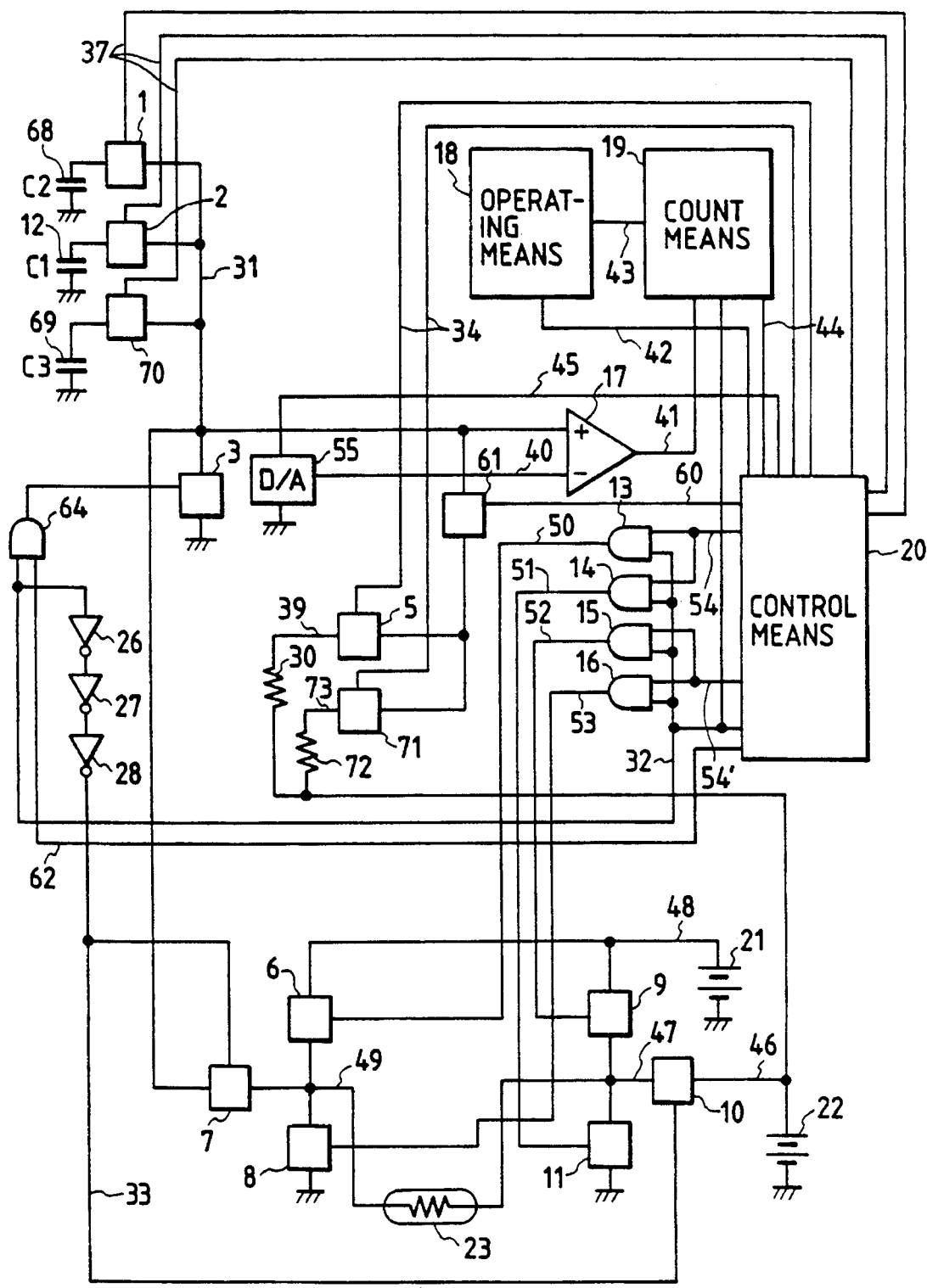
FIG. 5 shows a circuit configuration of a second embodiment of the present invention.
Figure 19:
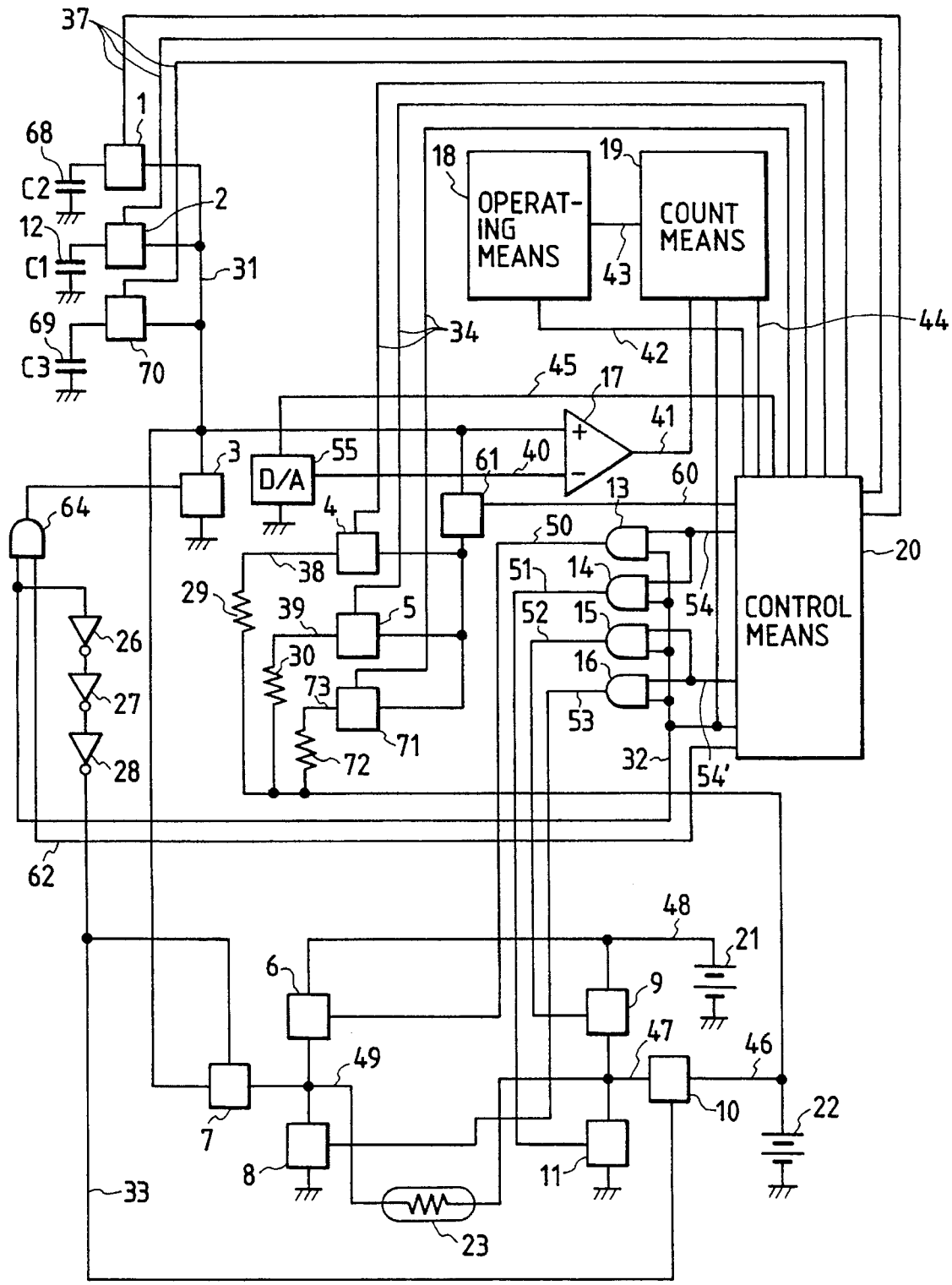
FIG. 19 shows another prior art circuit configuration.

FIG. 5 shows a circuit configuration of a second embodiment of the present invention. The like numerals to those of FIG. 19 designate the like elements. In FIG. 5, numerals 1–11 and 61 denote analog switches for switching paths of the circuits, which disconnect a humidity sensor 23 (corresponding to the humidity sensor 104 of FIG. 1) having the resistance thereof changed with a humidity from the circuit in the non-measurement mode, apply a signal of a square wave derived by inverting a reference DC voltage from a reference supply 21 at a fixed interval, switch the circuit such that capacitors 12, 68, and 69 are charged through comparison resistors 30 and 72 and discharge the charges stored in the capacitors 12, 68, and 69. In the measurement mode, the connect one end of the humidity sensor 23 to a reference supply 22 which generates a different reference DC voltage, connect the other end to the capacitors 12, 68, and 69 having the capacitances of C1, C2, and C3, and when the switch 7 is off, connect the reference resistors 30 and 72 to the capacitors 12, 68, and 69.

Numerals 13–16 denote AND gates which are used to control the switching timing of the analog switches 6, 8, 9, and 11. Numerals 21 and 22 denote the reference supplies which are of fixed voltage. Numeral 55 denotes a D/A converter for outputting a comparison reference voltage (voltage) of a comparator used in measuring the resistance of the humidity sensor 23. When a control signal is sent from control means 20 (corresponding to the detection means 113 in FIG. 1) which serially checks the respective means to a signal line 45, the output digital data is switched.

Numeral 19 denotes count means for counting charging times of the capacitors 12, 68, and 69. Operation means 18 calculates a humidity surrounding the humidity sensor 23 based on the count of the count means 19. Numerals 26, 27, and 29 denote inverter circuits which comprise devices to invert the input thereto. Those units are connected in the following manner.

One end of each of the capacitors 12, 68, and 69 having the other end thereof grounded is connected to one end of each of the analog switches 1, 2, and 70, and the other end of each of the analog switches 1, 2 and 70 is connected to the signal line 31, and through the signal line 31, to a positive input terminal of the comparator 17, a signal input terminal of the analog switch 3 having the other end thereof grounded, and one signal input terminal of the analog switch 7.

One signal input terminal of each of the analog switches 5 and 71 is connected to one end of each of the reference resistors 30 and 72 having the other end thereof grounded. A control terminal of the analog switch 61 is connected to the control means 20 through a signal line 60.

An analog signal output terminal of the D/A converter 55 is connected to a negative signal input terminal of the comparator 17 through a signal line 40. One signal input terminal of the analog switch 8 having the other signal input terminal grounded thereof is connected to one input signal terminal of each of the analog switches 6 and 7 and one terminal of the humidity sensor 23, and one input signal terminal of the analog switch 11 having the other input signal terminal grounded is connected to one signal input terminal of each of the analog switches 9 and 10 and the other terminal of the humidity sensor 23. The other signal input terminal of each of the analog switches 6 and 9 is connected to a positive terminal of the reference supply 21 having a negative terminal thereof grounded through a signal line 48, and the other signal input terminal of the analog switch 10 is connected to a positive terminal of the reference supply 22 having a negative terminal thereof grounded through a signal line 46.

A control terminal of the analog switch 1 is connected to a control signal output terminal of the control means 20 through a signal line 37. Signal lines 34 are connected to the control terminals of the analog switches 5 and 71. Control terminals of the analog switches 7 and 10 are connected to the output terminal of the inverter 28 through a signal line 33. Control terminals of the analog switches 6, 8, 9, and 11 are connected to the output terminals of 2-input AND gates 13–16, respectively. Similarly, the other signal input terminals of the AND gates 15 and 16 are connected to the control signal output terminal of the control means 20 through a signal line 54'.

A signal line 32 is connected to one input terminal of the 2-input AND gate 64 and an input terminal of the inverter 26. Three inverters 26, 27 and 28 form a delay element, and a signal output terminal of the inverter 26 is connected to a signal input terminal of the inverter 27 and a signal output terminal of the inverter 27 is connected to a signal input terminal of the inverter 28. A signal output terminal of the comparator 17 is connected to a signal input terminal of the count means 19 through a signal line 41.

The count means 19 and the control means 20 are connected through a bilateral signal line 44, and the count means 19 outputs operation information to the operation means 18 through a signal line 43. The operation means 18 is connected to a control signal output terminal of the control means 20 through a signal line 42. A control signal output terminal of the count means 19 is connected to a signal line 32 and one signal input terminal of the 2-input AND gate 64 is connected to a signal line 62. An output terminal of the AND gate 64 is connected to a control terminal of the analog switch 3.

The analog switches 5 and 71 and the reference resistors 30 and 72 are connected through signal lines 39 and 73 and the analog switches 6 and 9 are connected to the reference supply 21 through a signal line 48. One end of each of the analog switches 6, 7, and 8 is connected to the humidity sensor 23 through a signal line 49 and the other end of the analog switches 9, 10 and 11 are connected to the humidity sensor 23 through a signal line 47. Output terminals of the AND gates 13–16 are connected to the analog switches 6, 11, 9, and 8, respectively, through signal lines 50–53.

The comparator 17 compares the terminal voltages of the charging capacitors 12, 68, and 69 with the threshold voltage of the reference supply (D/A converter 55) which is adjustable by setting, and the count means 19 measures the charging time from the start point of measurement to the arrival to the present threshold, that is, the time from the start of measurement to the change of the output signal of the comparator 17. The humidity surrounding the humidity sensor 23 is determined by the operation means 18 based on the result of measurement.

Figure 6:
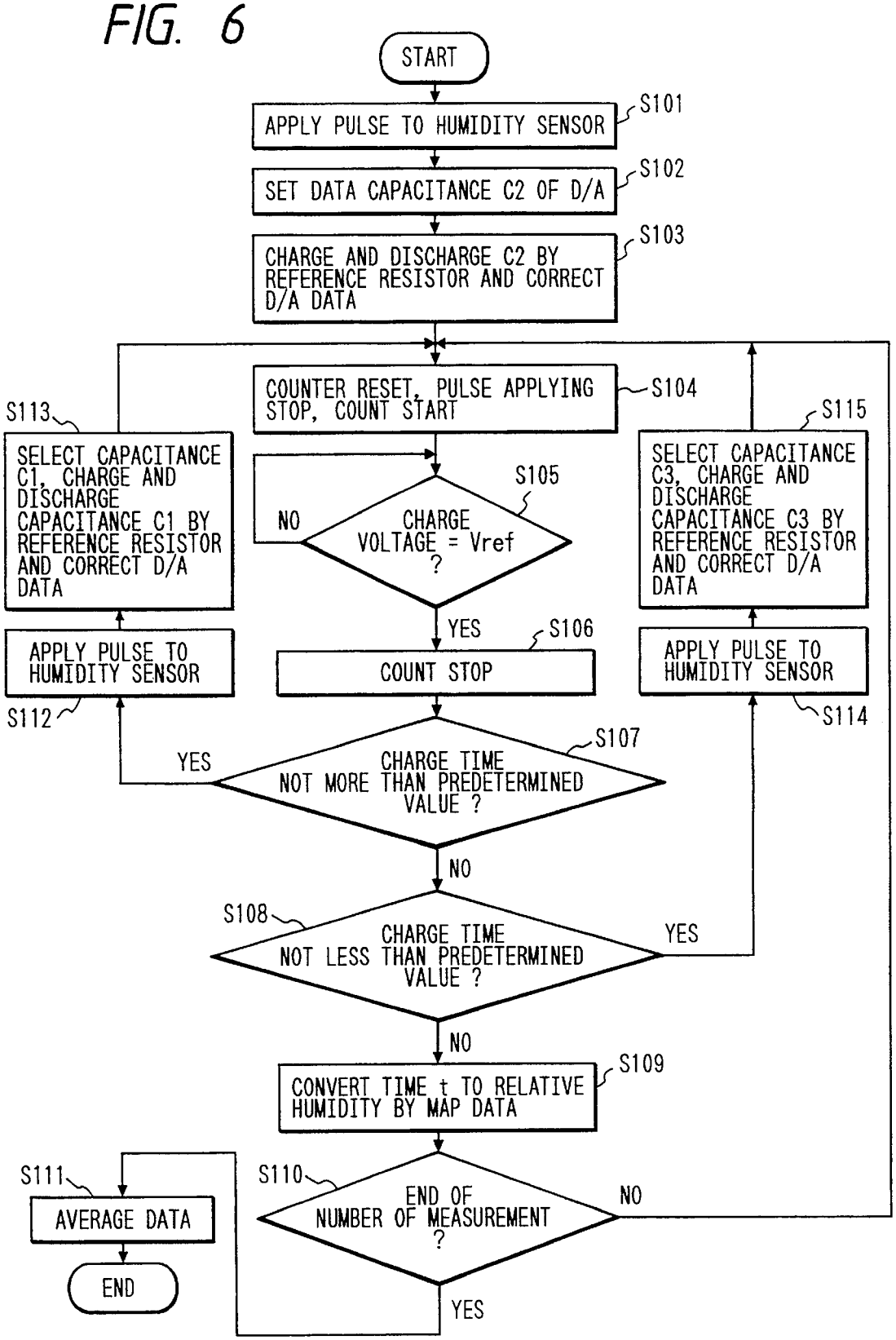
FIG. 6 shows a flow chart of a measurement operation of the second embodiment.
Figure 20:
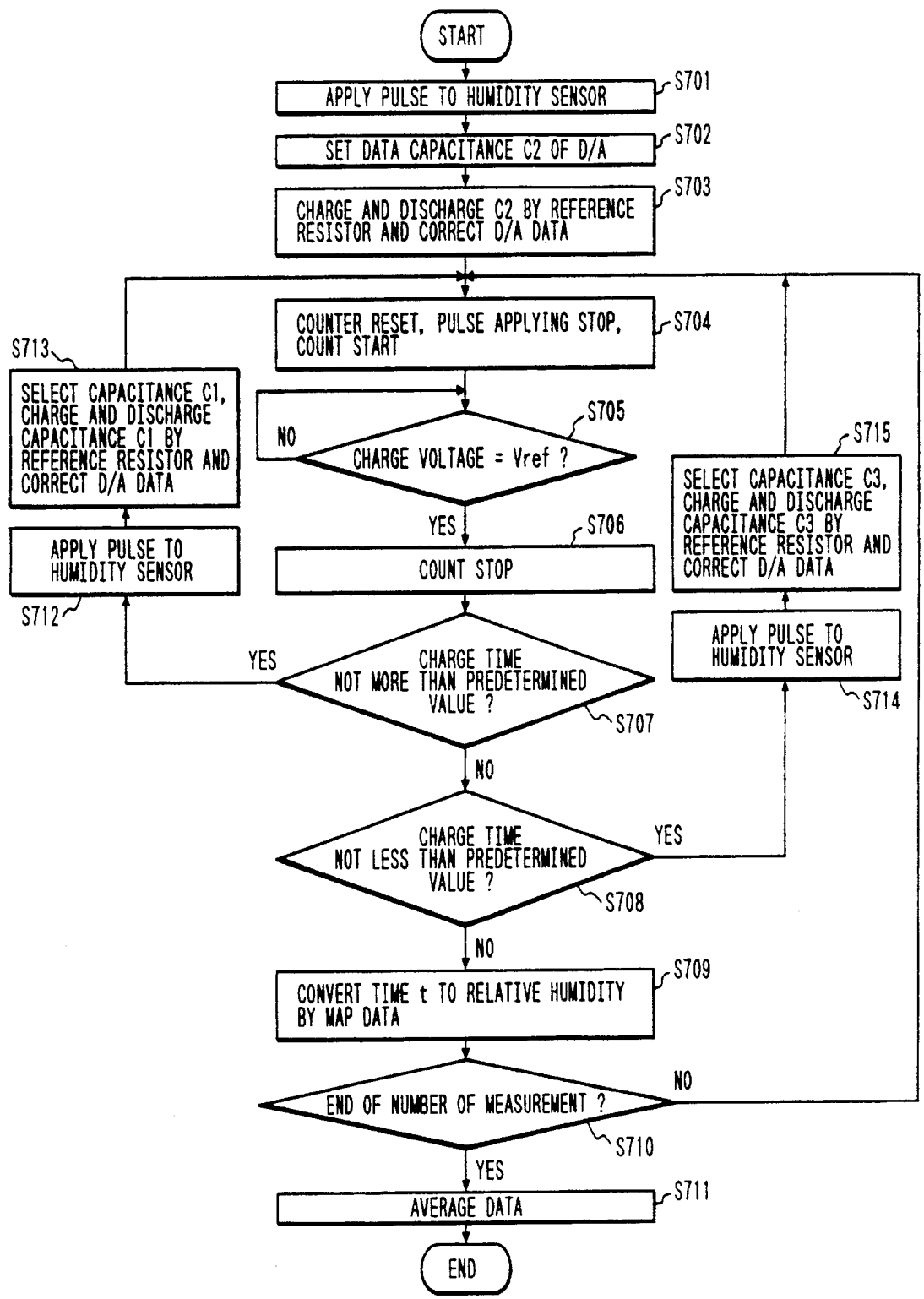
FIG. 20 shows a flow chart of an operation of the circuit of FIG. 19.
Figure 21:
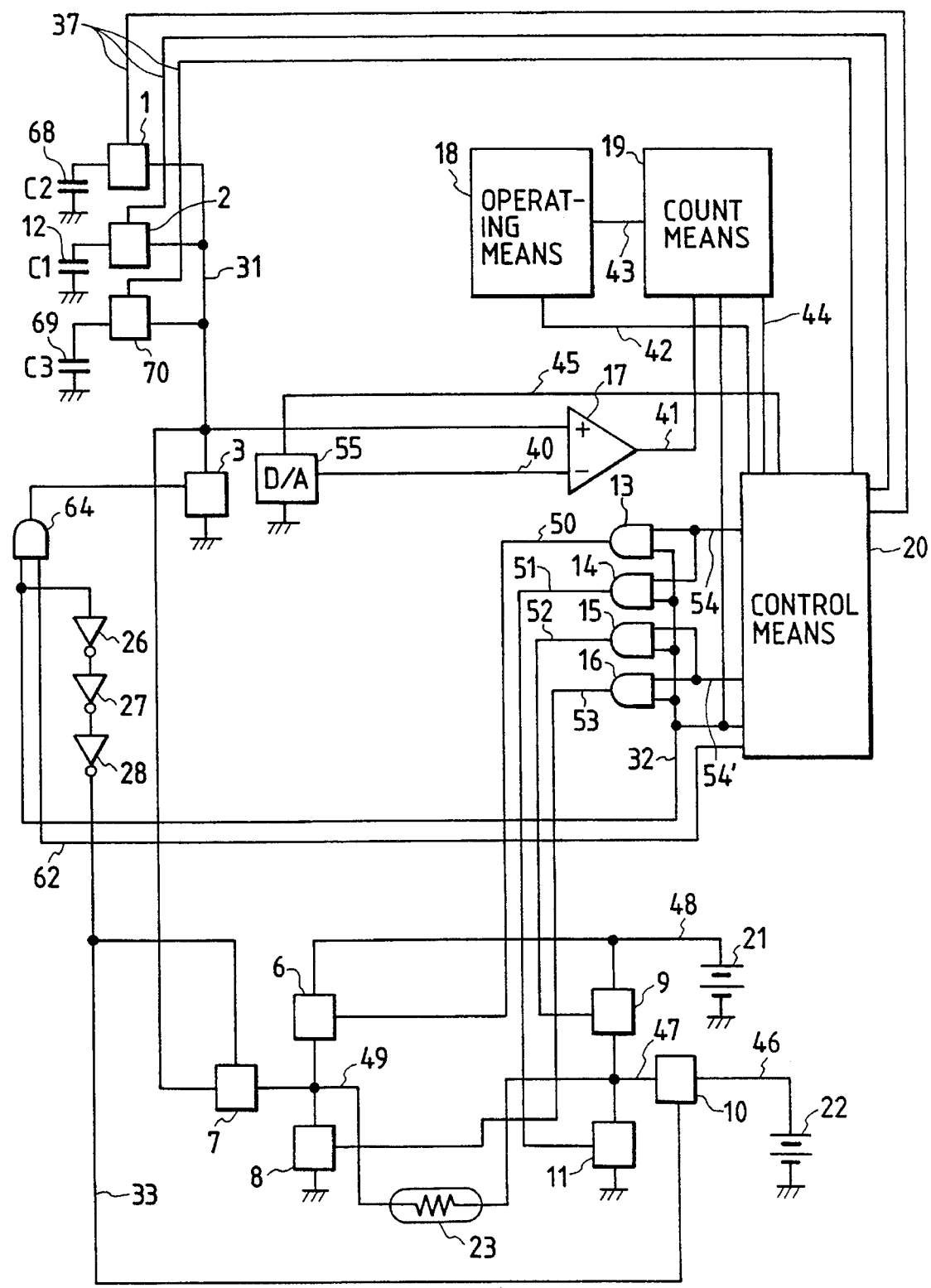
FIG. 21 shows another prior art circuit configuration.

FIG. 6 shows a flow chart of the measurement operation in the second embodiment. The contents of the steps S101–S115 are identical to those of the steps S701–S715 of FIG. 20. Only a characteristic portion of the present embodiment is described below.

In the prior art, the capacitance C2 is set to approximately 6800 pF which fits to the middle humidity range measurement, the capacitance C1 is set to approximately 0.68 μF which fits to the high humidity range measurement, the capacitance C3 is set to approximately 33 pF which fits to the low humidity range measurement, and the resistances of the resistors 29, 30, and 72 are set to 1 KΩ, 100 KΩ, and 10 MΩ, respectively with a precision of no greater than ±1% to define the time constants with C1, C2, and C3. When a voltage level (for example, 0.2 V) is applied to the negative terminal of the comparator 17 and the voltage (for example, 1 V) of the reference supply 22 is applied to the respective resistors under this condition, the time to charge the capacitance is 100μ seconds. The charging is effected before the capacitance is charged by the humidity sensor 23 and the digital data of the D/A converter 55 is changed to compensate for a deviation from 100μ seconds as a reference.

In the present embodiment, one of the three reference resistors (for example, 1 KΩ or 100 KΩ) is eliminated and the pair of capacitances to be compensated are compared with the charging time of 10 m seconds with two-order higher reference resistance to change the digital data of the D/A converter 55.

Namely, the measurement range of the humidity is divided into at least three as an environment condition, and a reference resistor for compensating the capacitance of the capacitor is provided for each range and at least two of them are shared. Accordingly, the analog switches therefor can be reduced and the cost can be reduced.

Figure 7:
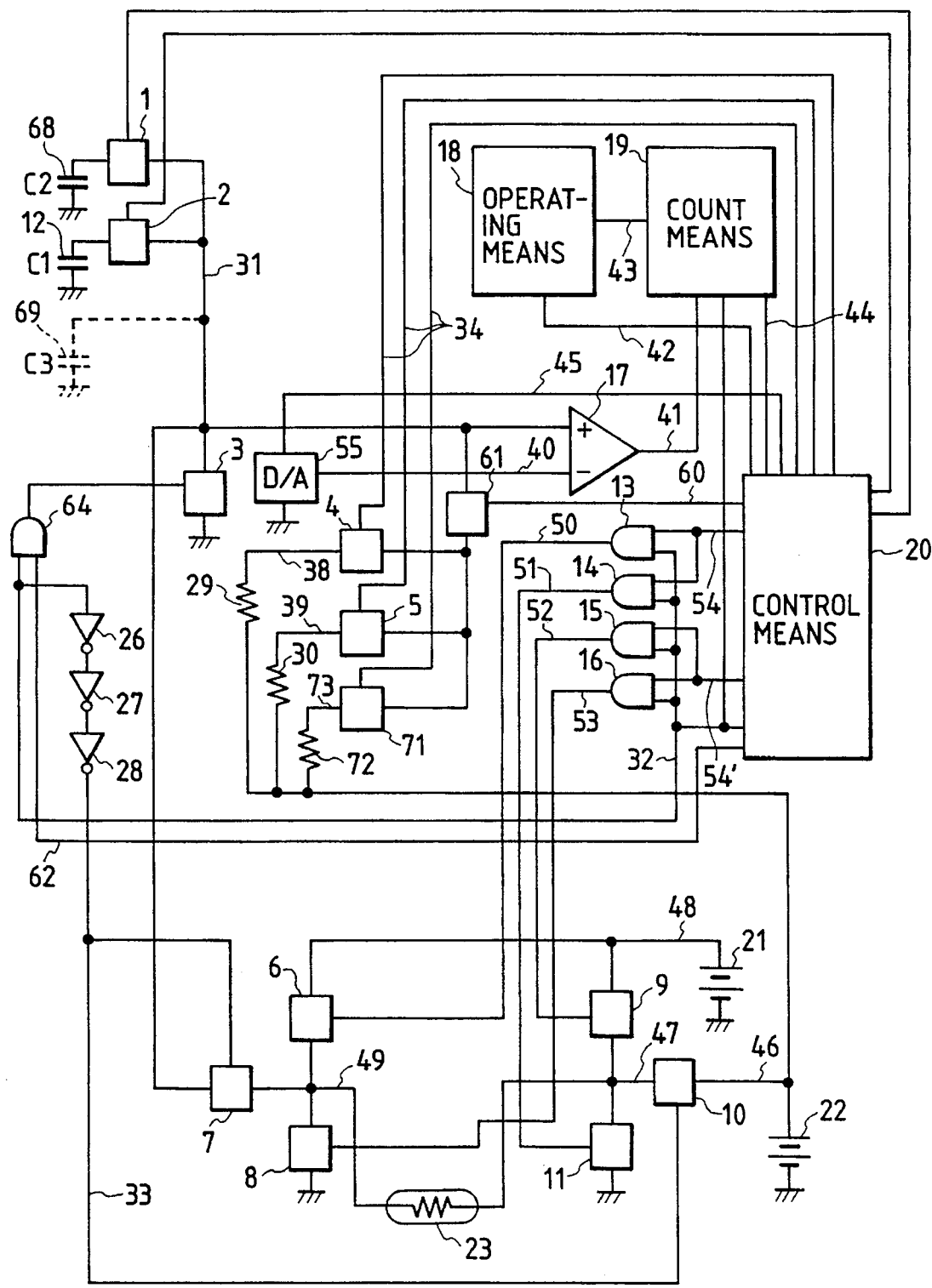
FIG. 7 shows a circuit configuration of a third embodiment of the present invention.

FIG. 7 shows a circuit configuration of a third embodiment of the present invention. In the present embodiment, a capacitance (C3) for measuring the environment condition in which the humidity sensor 23 exhibits a high resistance is a capacitance (stray capacitance) included in the apparatus.

Figure 8:
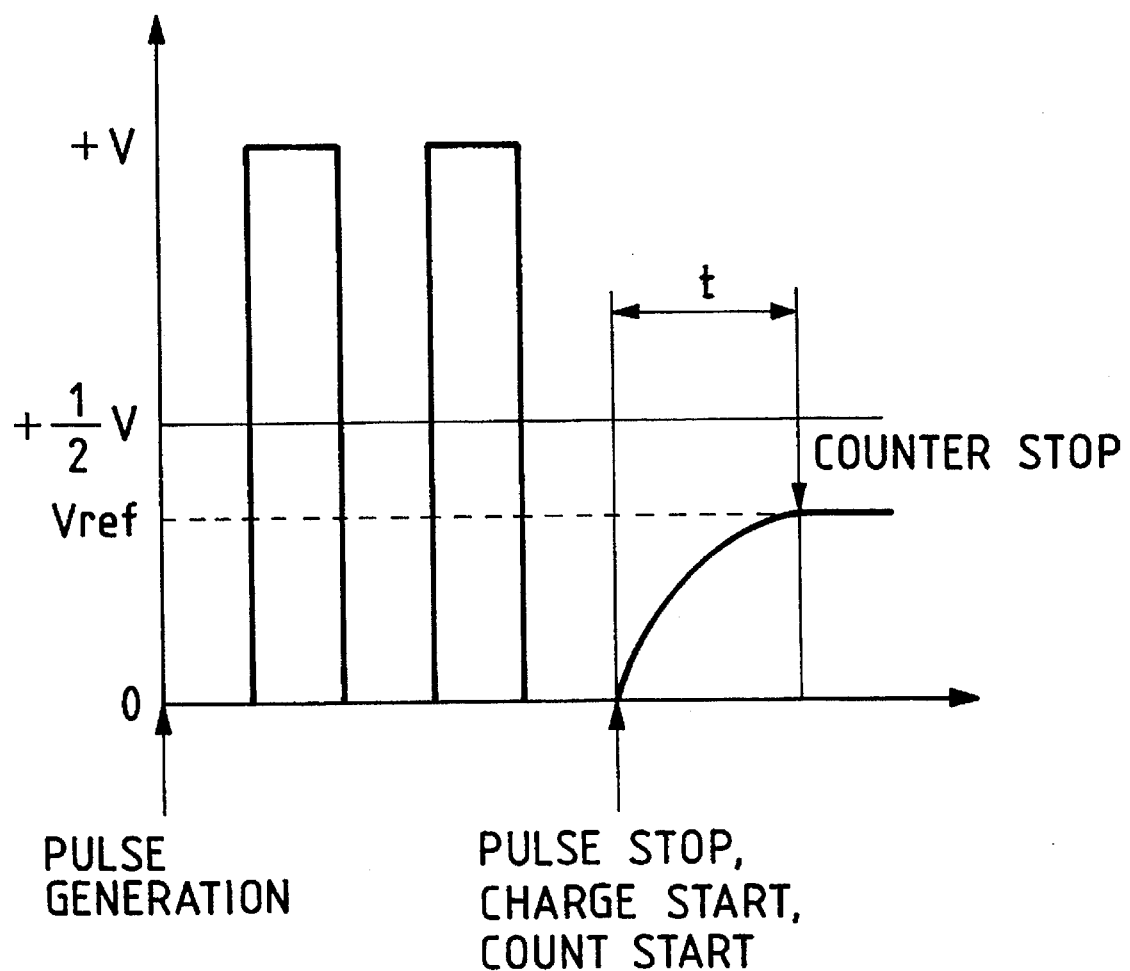
FIG. 8 shows pulse waveforms applied to a humidity sensor of FIG. 7.
Figure 9:
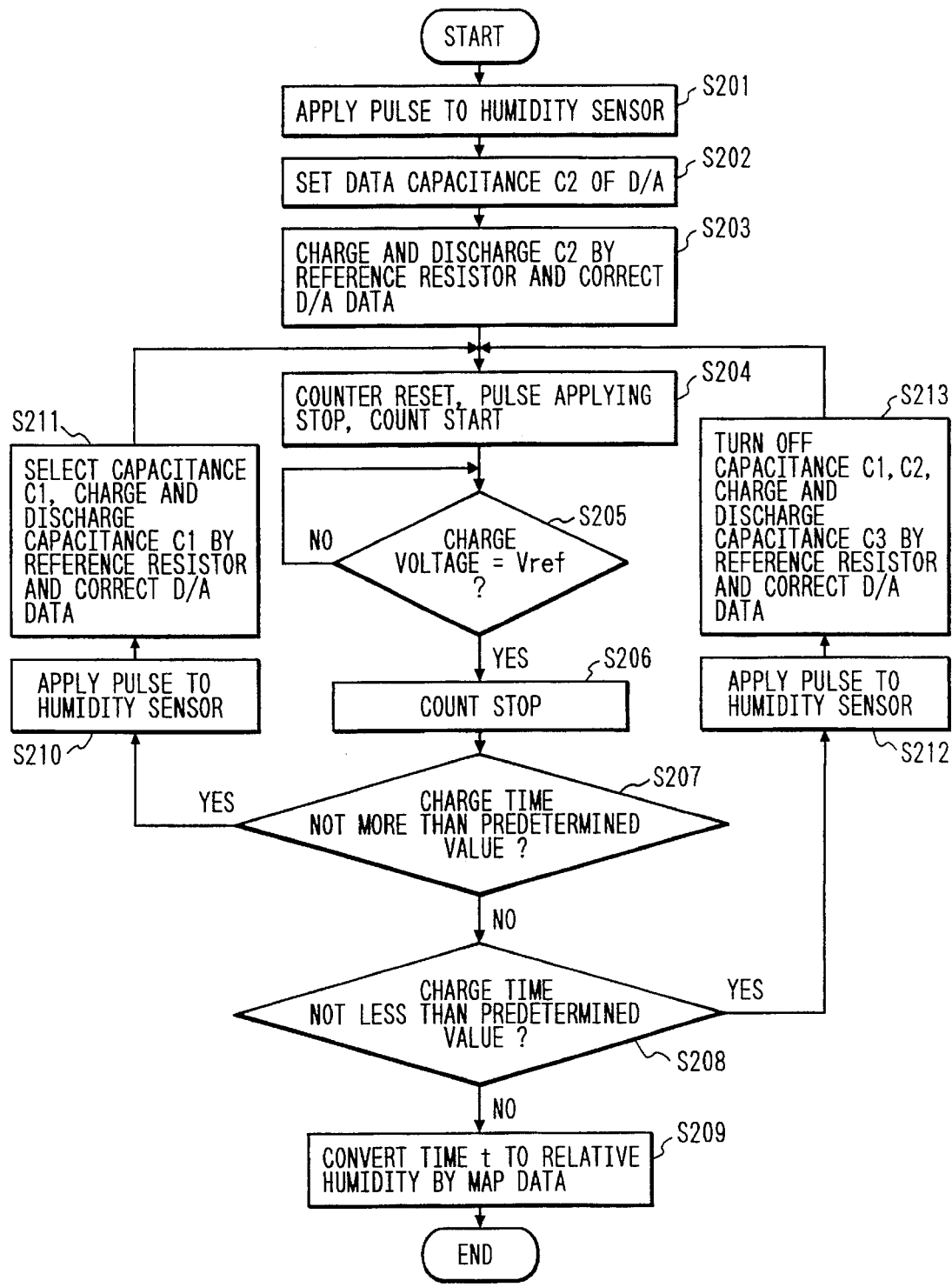
FIG. 9 shows a flow chart of a measurement operation of the third embodiment.

FIG. 8 shows a pulse waveform chart applied to the humidity sensor 23 of FIG. 7, and FIG. 9 shows a flow chart of a measurement operation in the present embodiment as shown in FIG. 7.

In the flow chart of FIG. 9, steps S201–S209 correspond to the steps S101–S109 of FIG. 6, and steps S210 and S211 and steps S212 and S213 correspond to the steps S112 and S113 and the steps S114 and S115. Therefore, the explanation of those steps is omitted.

In the prior art, since a capacitance of approximately 10 pF is inherently included between the analog switch and the circuit board, if ten or more analog switches are connected to the capacitor under the environment condition in which the resistance of the humidity sensor 23 is several GΩ, the measurable range is narrowed by the increase of the capacitance. In the present embodiment, by using only the capacitance between the analog switch and the circuit board of the apparatus to charge and discharge under the environment condition in which the resistance of the humidity sensor 23 is several GΩ, the measurable range of the environment condition is expanded and the cost is reduced.

Figure 10:
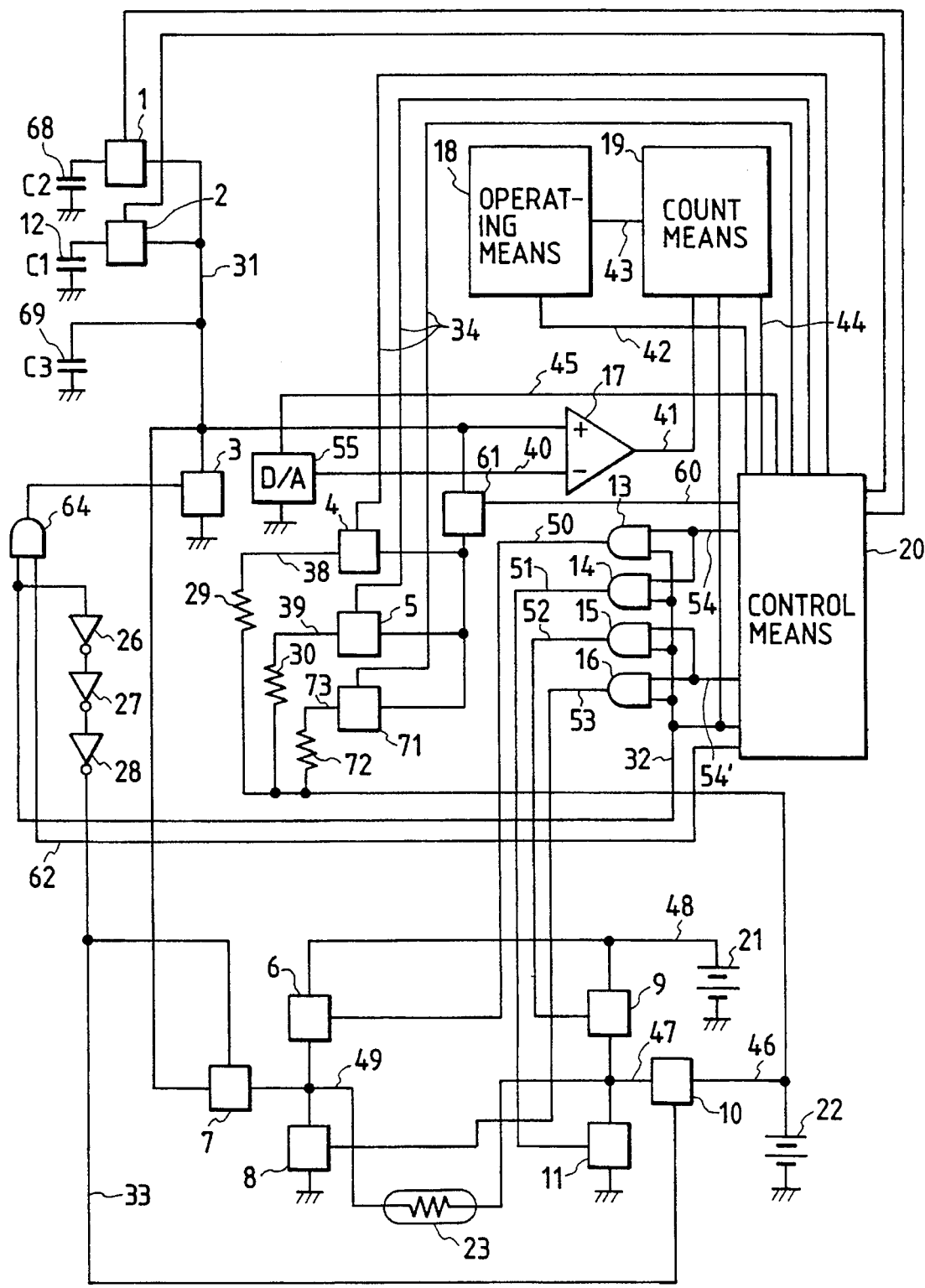
FIG. 10 shows a circuit configuration of a fourth embodiment of the present invention.

FIG. 10 shows a circuit configuration of a fourth embodiment of the present invention. In the present embodiment, higher precision measurement in the low humidity range than that of the third embodiment is attained. The capacitance (C3) to measure the environment condition in which the resistance of the humidity sensor 23 is high is always connected to the humidity sensor 23.

In the embodiment of FIG. 7, the capacitance (C3) which is present between the analog switch and the circuit board of the apparatus to measure the low humidity range may vary with a measurement condition. Thus, in order to reduce the variation of the capacitance, the capacitance (C3) is connected to the signal line 31 in the present embodiment and it is not connected to the humidity sensor 23 in series through the analog switch but it is directly connected to the humidity sensor 23. The capacitance (C3) may, for example, by approximately 100 pF.

In this manner, the capacitance switched by the analog switch in the previous embodiment is directly connected in series with the humidity sensor 23 in the vicinity of the input terminal of the comparator 17 in the apparatus, the affect of the analog switch by the change of the capacitance is reduced and the cost is reduced.

Figure 11:
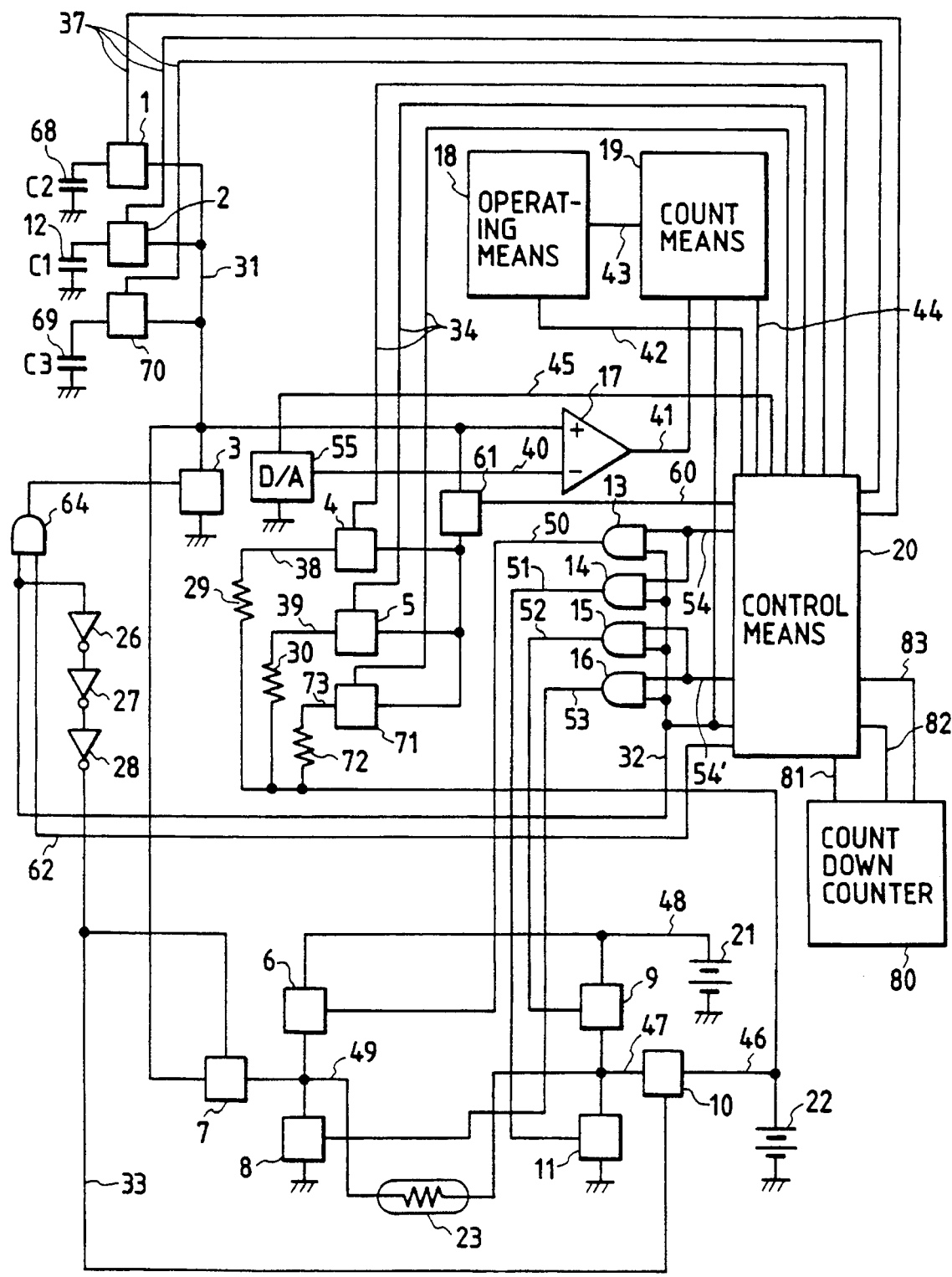
FIG. 11 shows a circuit configuration of a fifth embodiment of the present invention.

FIG. 11 shows a circuit configuration of a fifth embodiment of the present invention. In the present embodiment, the time interval of the repetitive measurement to the next measurement is varied in accordance with the charging time of the capacitors 12, 68 and 69. Specifically, a count-down counter 80 is provided.

The count-down counter 80 is connected to a humidity sensor relaxation time setting data output port of the control means 20 through a signal line 81, to a relaxation time count start signal output terminal through a signal line 82, and to a humidity sensor relaxation time end detection terminal through a signal line 83.

Figure 12B:
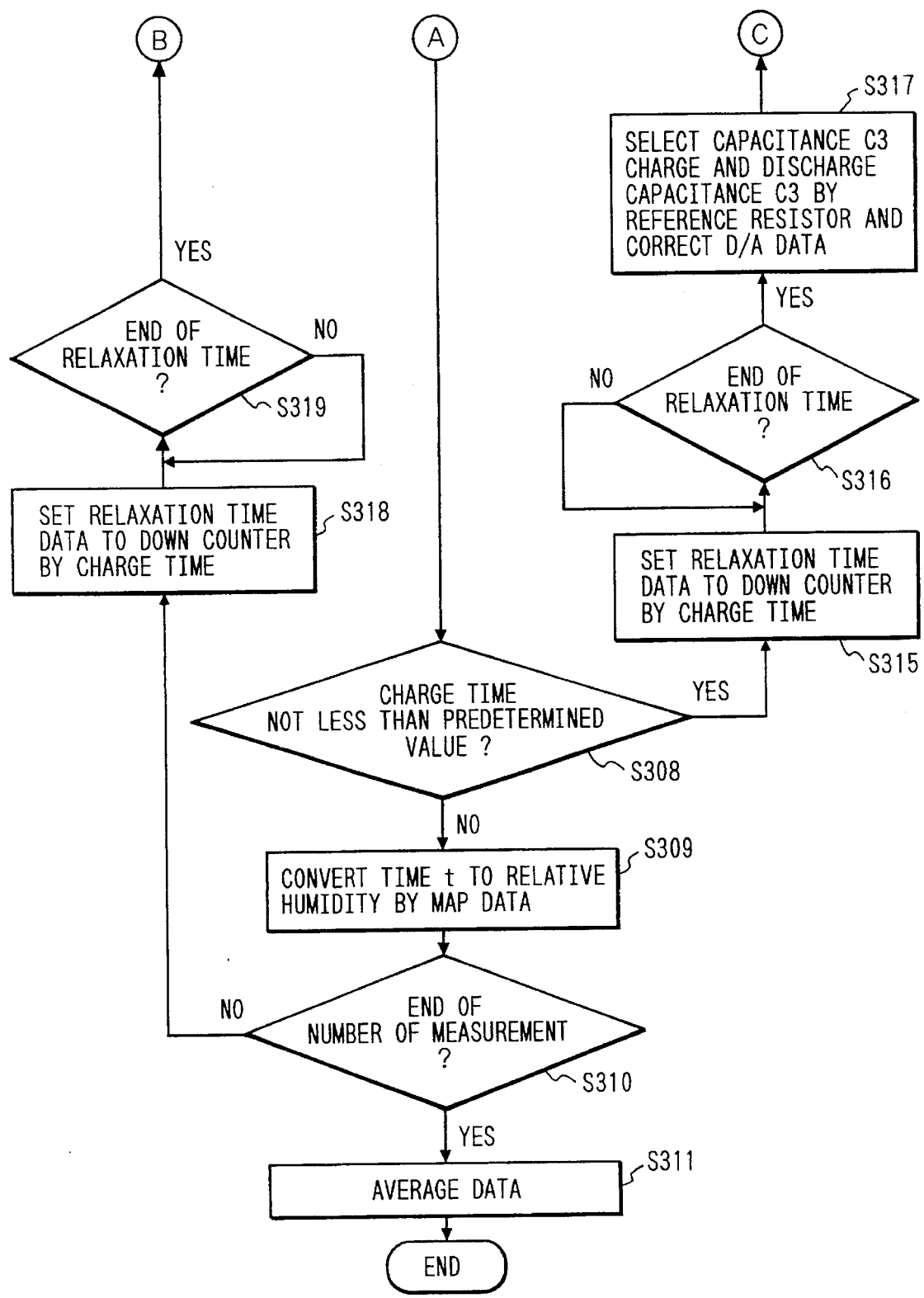
FIG. 12 is comprised of FIGS. 12A and 12B showing flow charts of a measurement operation of the fifth embodiment.

FIGS. 12A and 12B show a flow chart of a measurement operation of the fifth embodiment. Steps S301–S315 of the flow chart are identical to the steps S101–S111 of FIG. 6 and the explanation thereof is omitted. When the count of the count means 19 does not reach a predetermined level (for example, 100μ seconds), or within a predetermined range (for example, 100μ seconds–10 m seconds), the control means 20 receives the information through the signal line 44 and temporarily returns to the humidity non-measurement mode and outputs setting data to count a predetermined, relaxation time (for example, two seconds) through the signal line 81 (S312) and starts the count-down through the signal line 82. Then, when the set relaxation time is over (S313), the control means 20 detects the humidity sensor relaxation end through the signal line 83 and then selects the capacitance C1 to correct the D/A data (S314), and measures the humidity again.

When the count of the count means 19 does not reach the predetermined level (for example, 100μ seconds), the analog switch 2 is turned on to connect the capacitance C1 to the signal line 31, and when it is within the predetermined range (for example, 100μ seconds–10 seconds), the analog switch 1 is turned on to connect the capacitance C2 to the signal line 31, and the humidity measurement is repeated.

When the count of the count means 19 is above the predetermined level (for example, 10 m seconds), in accordance with a feature of the present embodiment, the control means 20 receives the information through the signal line 44 and temporarily returns to the humidity measurement mode and outputs setting data to count the predetermined relaxation time (for example, 10 seconds) to the count-down counter 80 through the signal line 81 (S315), and starts the down-counting through the signal line 82. Then, when the set relaxation time is over (S316), the control means 20 detects the humidity sensor relaxation time end through the signal line 83 and then selects the capacitance C3 to correct the A/D data (S317) and measures the humidity again.

At this time, the analog switch 70 is turned on to connect the capacitance C3 to the signal line 31 and the above humidity measurement is repeated. Before the above condition is modified for the remeasurement, the data of the D/A converter which supplies the reference potential to the negative input terminal of the comparator 17 is corrected in the manner described above (S318, S319).

In the above embodiment, the humidity sensor relaxation time between environment measurements may be linearly varied in accordance with the data of the count means 19.

$$T = \alpha Tx + \beta$$

where

T: humidity sensor relaxation time setting data

Tx: data of the count means 19

α,β: constants

Namely, when the data of the count means 19 in the previous environment measurement is small, the humidity sensor relaxation time is set short, and when the data of the count means 19 is large, the humidity sensor relaxation time is set long so that the environment measurement time per se is shortened and the deterioration of the humidity sensor as the number of times of environment measurement increases is avoided and the performance of the apparatus can be maintained over an extended period.

In the prior art, the remeasurement of humidity is effected by setting the non-measurement time to relieve the deterioration of the humidity sensor 23 at each end of the measurement to a fixed time to prevent the deterioration of the performance by the application of the excessive DC voltage to the humidity sensor 23. However, the finding by the experiment by present inventors is that the initial performance of the humidity sensor 23 is not restored unless the relaxation time is set 10 seconds or longer, the humidity sensor 23 is deteriorated as the number of times of environment measurement increases and it is not possible to maintain the performance of the environment measurement apparatus over the extended period. However, in the present embodiment, the humidity sensor's relaxation time is variably set in accordance with the length of the previous measurement time after the completion of each humidity measurement so that the performance of the environment measurement apparatus per se is maintained over the extended period without deterioration of the humidity sensor 23 even if the number of times of environment measurement increases.

Figure 13:
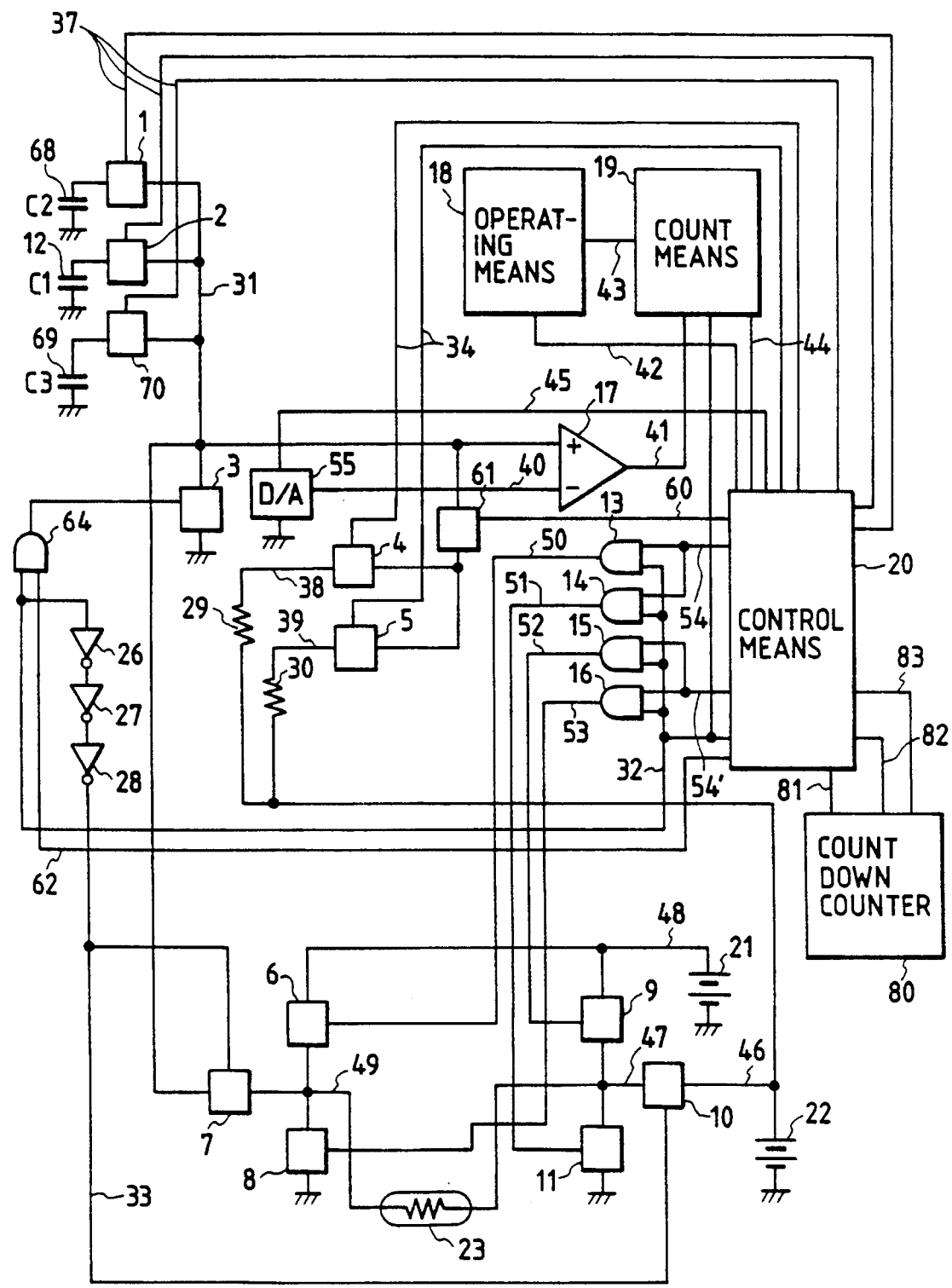
FIG. 13 shows a circuit configuration of a sixth embodiment.
Figure 14:
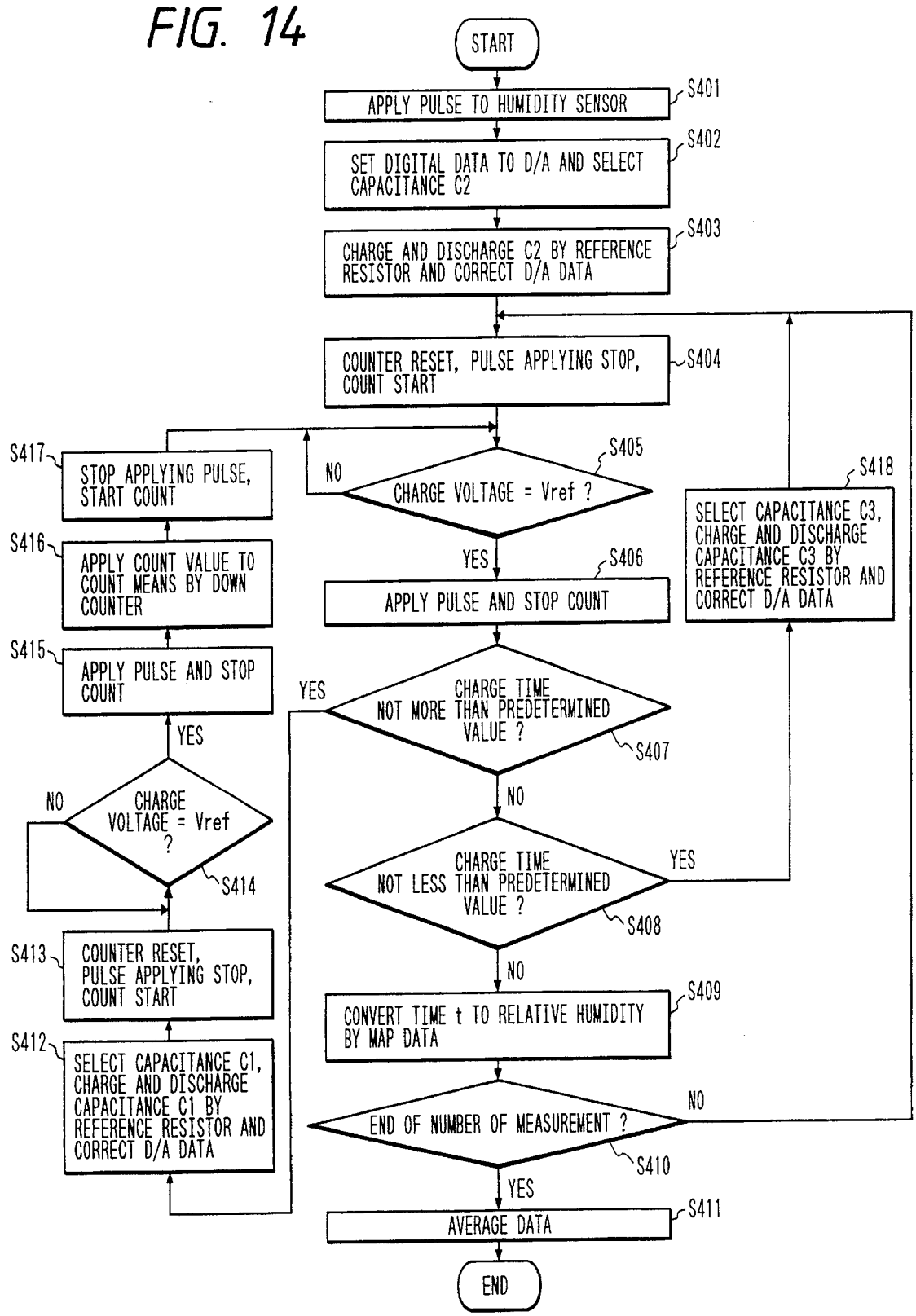
FIG. 14 shows a flow chart of a measurement operation of the sixth embodiment.
Figure 15:
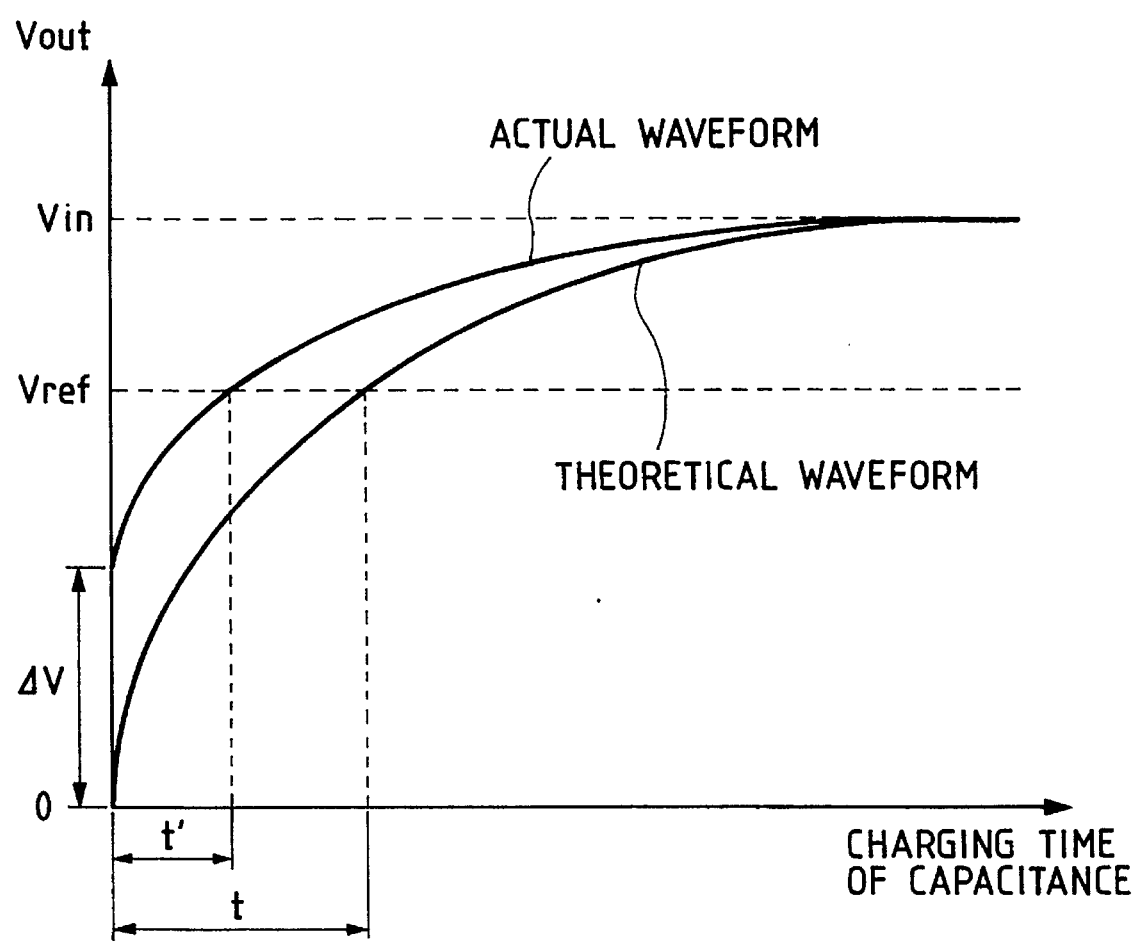
FIG. 15 shows a voltage waveform at a positive input terminal of a comparator.

FIG. 13 shows a circuit configuration of a sixth embodiment of the present invention. In the present embodiment, when the environment condition (humidity) in which the humidity sensor exhibits a low resistance is to be measured, an offset measurement is applied to the count means which is the measurement means for the charging time of the capacitor to compensate it. A measurement operation is shown in FIG. 14. FIG. 15 shows a voltage waveform at the positive input terminal of the comparator 17 of FIG. 13.

In the flow chart of FIG. 14, steps S401–S411 are identical to the steps S101–S111 of FIG. 6. A characteristic compensation operation of the present embodiment is explained below.

Under the high humidity condition (environment condition in which the humidity sensor 23 exhibits a low resistance), the analog switch is turned on to charge the capacitance C1 by the humidity sensor 23.

The analog switches 2 and 3 are first turned on to discharge the capacitance C1 to render the positive input terminal of the comparator 17 to GND potential. The analog switch 3 is turned off and the analog switches 61 and 4 are turned on to charge the capacitance C1 through the reference resistor 29, and the time to the inversion of the output of the comparator 17 is measured by the count means 19. The charging time is compared with a theoretical time to compensate the digital data of the D/A converter 55 (S412, S418).

Then, the analog switches 4 and 61 are turned off and the signal lines 32 and 62 are rendered to "L" to charge the capacitance C1 through the humidity sensor 23 and the charging time is measured (S413–S415). Immediately before the start of the measurement, the potential at the positive input terminal of the comparator 17 is slightly raised by the resistor division by the humidity sensor 23 and the on-resistance of the analog switch 22 as shown in FIG. 15.

In order to eliminate the offset potential at the positive input terminal of the comparator 17, after the measurement of the charging time by the count means, the offset count of the count means 19 is determined by the control means 20 and it is set to the count-down counter 80 (S416). The count means 19 and the count-down counter 80 are simultaneously started (S417), and when the count end signal is outputted from the count-down counter 80 to the control means 20, the control means 20 applies the count stop signal to the count means 19 so that the offset count is applied to the count means 19.

The compensation in the remeasurement of humidity is effected. A method for calculating the offset count determined by the control means 20 is now explained.

Assuming that the reference supply 21 is Vin, the voltage across the capacitance C1 is Vc, the voltage applied to the positive input terminal of the comparator 17 is Vout, the resistance of the humidity sensor 23 is R, the on-resistance of the analog switch 2 is Rz, the measured charging time is t', the theoretical charging time is t and the capacitance of the capacitor C1 is C, $$Vc=Vin*(1-e^{-t'/((R+Rz)c)})$$

$$Vout=(Vin-Vc)*Rz/(R+Rz)+Vc$$

$$Vout=\{Vin-Vin(1-e^{-t'/((R+Rz)C)})\}*Rz/(R+Rz)+Vc$$

Thus, the measured charging time is determined by the following formula assuming Vout=Vref (negative input terminal voltage of the comparator 17):

$$t'=C(R+Rz)*1n\{(Rz/(R+Rz))*(Vin/(Vin-Vref))\} \quad (1)$$

The theoretical charging time t is given by $$t=CR1n(Vin/(Vin-Vref) \quad (2)$$

Assuming $$Vin/(Vin-Vref)=Y,$$

$$t-t'=C(Rin((R+Rz)/R)-YRz1n(R/(R+Rz))) \quad (3)$$

The formula (1) indicates that a linear approximation may be made in the range of 4 KΩ–10 KΩ of the humidity sensor 23 in the high humidity condition. Accordingly, $$t'=f(R) \rightarrow R=g(t')$$

where f and g are linear functions.
The formula (3) indicates that the linear approximation may be made in the range of 4 KΩ–10 KΩ of the humidity sensor 23. Accordingly, $$t-t'(\text{offset count})=f(g(t'))$$

Thus, the offset count may be represented by a linear function of t'.

Figure 16:
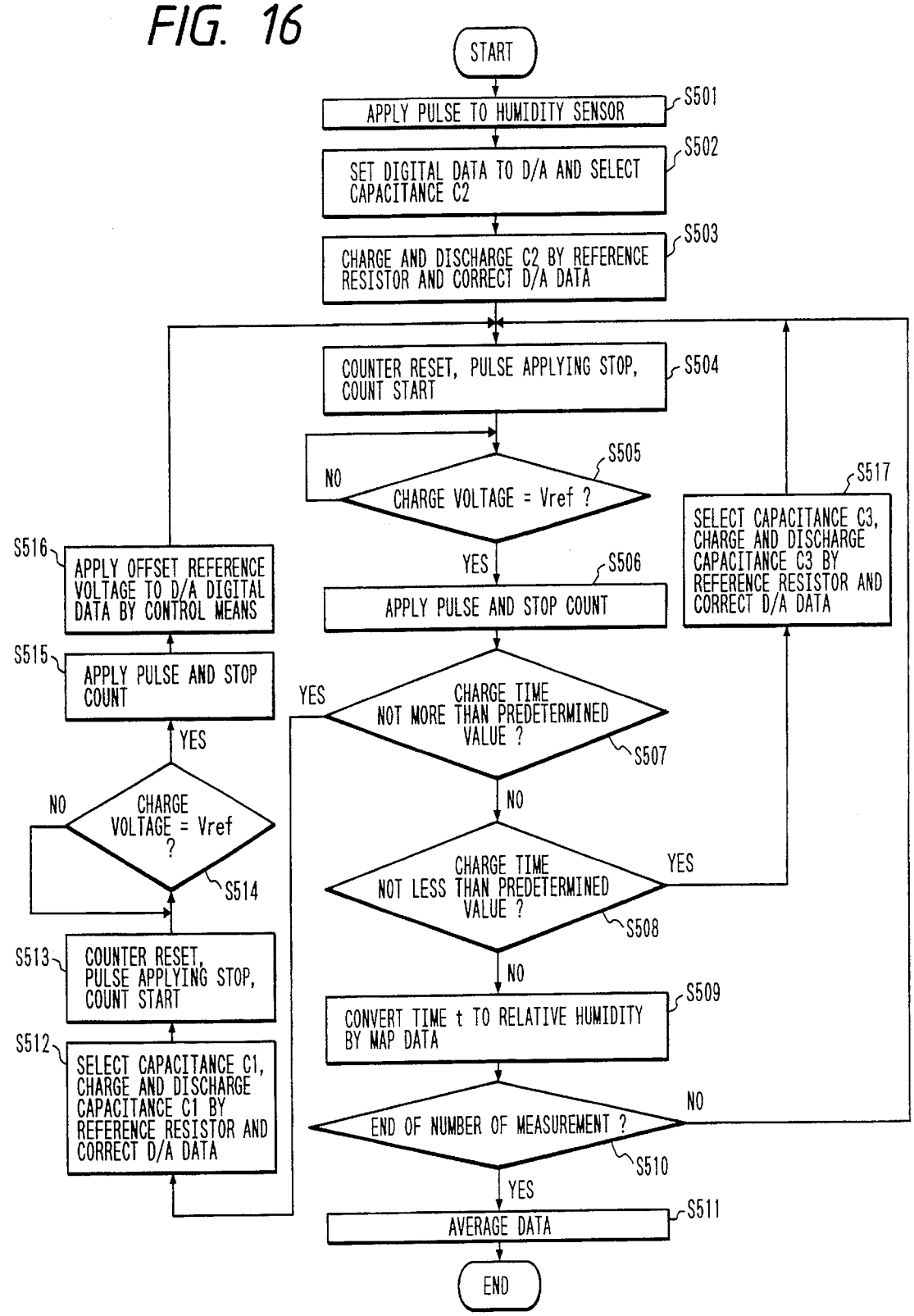
FIG. 16 shows a flow chart of a measurement operation of a seventh embodiment.

FIG. 16 shows a flow chart of a measurement operation of a seventh embodiment of the present invention. A circuit configuration of the present embodiment is identical to that of FIG. 5 and it is omitted. Steps S501–S516 in the flow chart of FIG. 16 are identical to the steps S401–S416 of FIG. 14 and a step S517 is identical to the step S418.

In accordance with a feature of the present embodiment, instead of applying the offset count to the count means 19, an offset voltage is applied to the digital data of the D/A converter 55 to eliminate the slight rise of the potential at the positive input terminal of the comparator by the resistor division by the humidity sensor and the on-resistance of the analog switch 24 which occurs immediately before the start of measurement.

From the above formulas (1) and (2), $$Vref=Vin(1-e^{-t/CR}) \quad (4)$$

$$Vref'=Vin(1-e^{-t/C(R+Rz)}+Rz/(R+Rz)e^{-t/C(R+Rz)}) \quad (5)$$

From the formulas (4) and (5), the offset voltage (Vref–Vref) applied to the digital data of the D/A converter 55 is given by $$Vref'-Vref \cong Rz/(R+Rz)*Vin*e^{-t/C(R+Rz)} \quad (6)$$

The formula (6) indicates that the linear approximation may be made in the range of 4 KΩ–10 KΩ of the humidity sensor 23.

From the sixth embodiment, $$R=g(t')$$

$$Vref'-Vref \text{ (offset voltage)}=q(g(t'))$$

where q is a linear function.
Thus, it is represented as a linear function of the offset voltage t' of the D/A converter 55.

Figure 17:
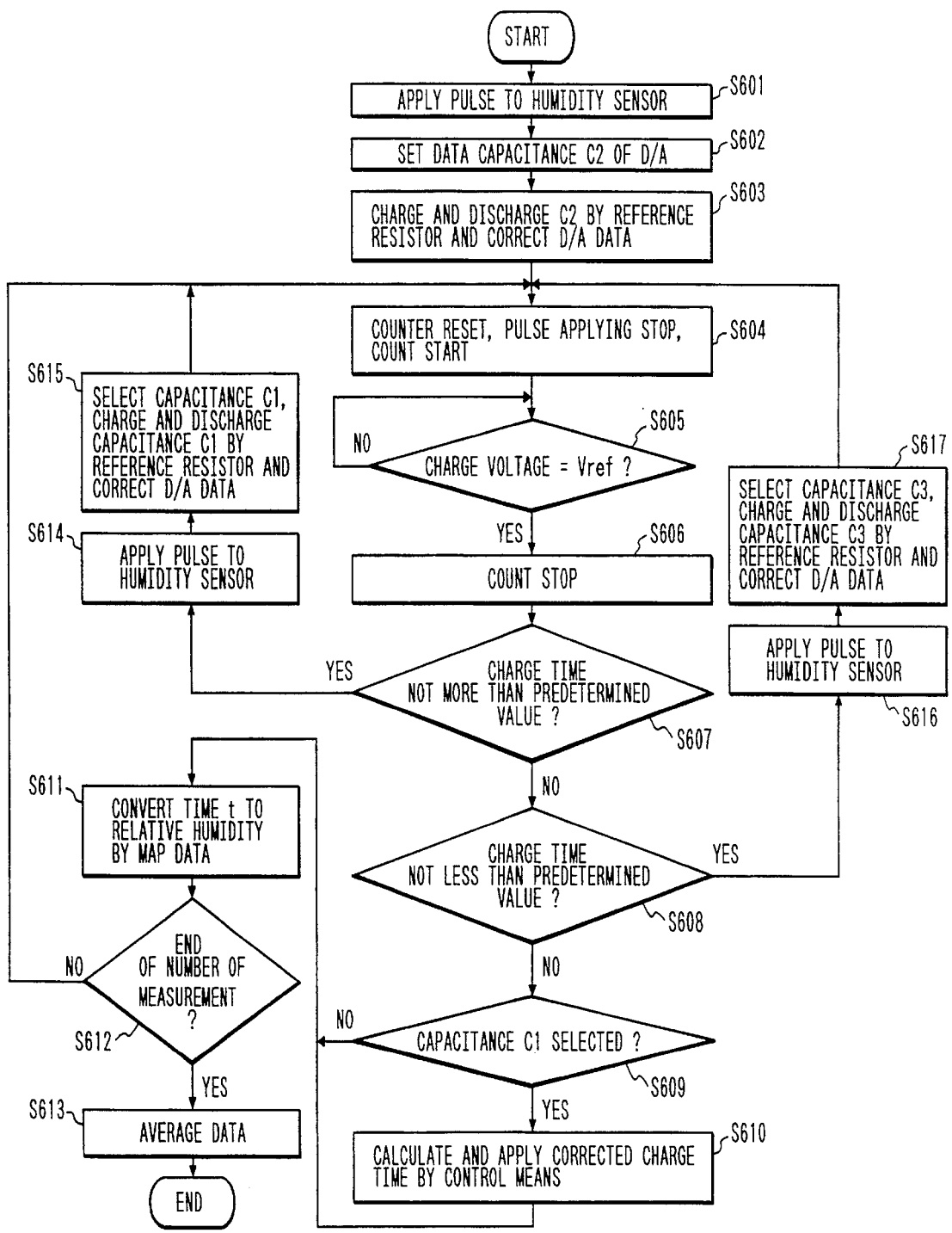
FIG. 17 shows a flow chart of a measurement operation of an eighth embodiment.
Figure 18:
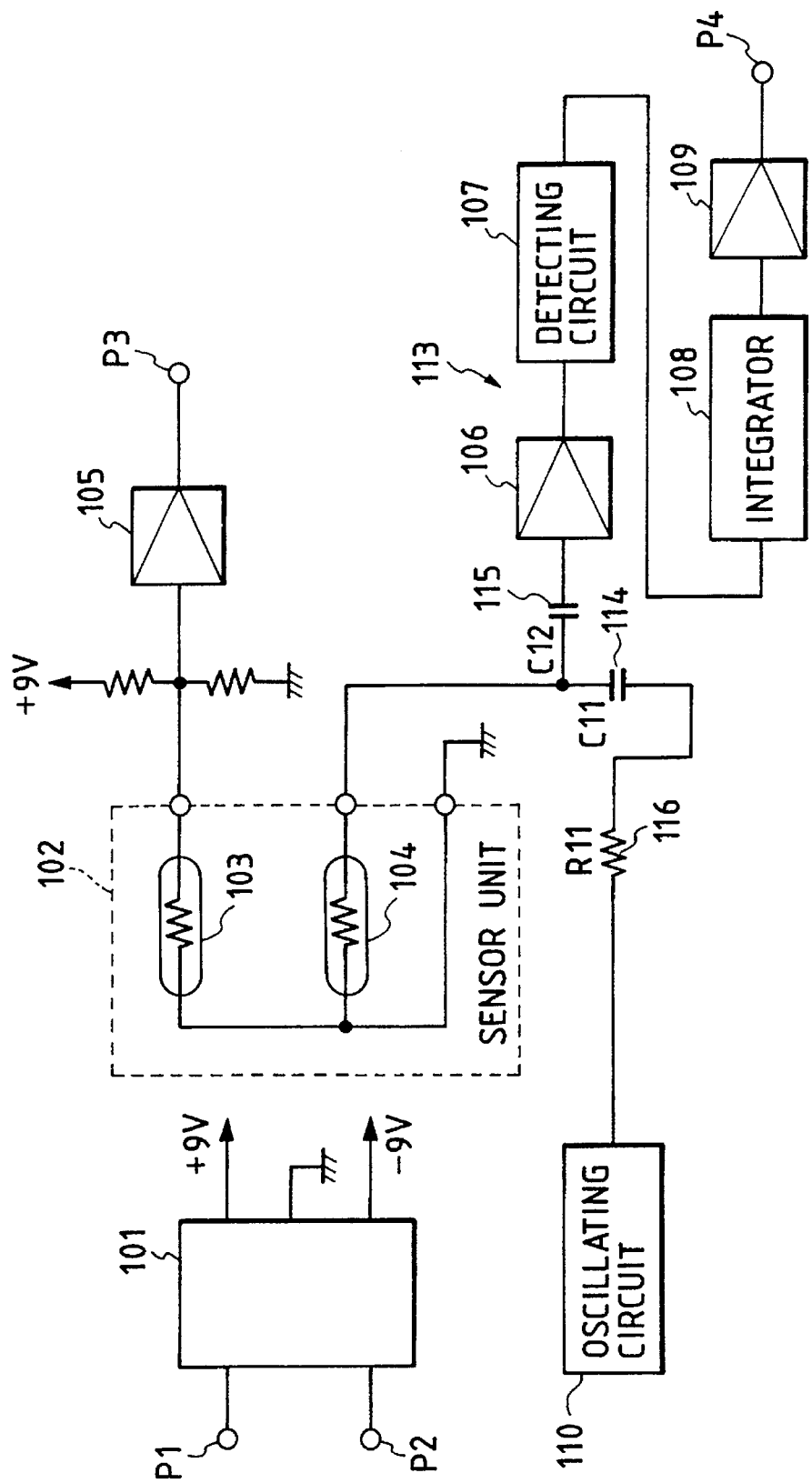
FIG. 18 shows a prior art circuit configuration.

FIG. 17 shows a flow chart of a measurement operation in an eighth embodiment of the present invention. In the flow chart, steps S601–S608 are identical to the steps S101–S108 of FIG. 6, steps S611–S613 are identical to the steps S109–S111, steps S614 and S615 are identical to the steps S112 and S113, and steps S616 and S617 are identical to the steps S114 and S115.

In accordance with a feature of the present embodiment, instead of applying the offset count to the count means 19 or applying the offset voltage to the digital data of the D/A converter 55, a compensation charging time calculated by the control means 20 is applied to the measured charging time to eliminate the slight rise of the potential at the positive input terminal of the comparator 17 by the resistor division by the humidity sensor 23 and the on-resistance of the analog switch 2 which occurs immediately before the start of measurement (S609, S610).

Assuming $$Vin/(Vin-Vref)=Y$$

from the formula (3), the compensation charging time is given by $$t-t'=C(R1n((R+Rz)/R-YRz1n(R/(R+Rz)))$$

In the prior art, in the environment condition (high humidity range) in which the humidity sensor 23 exhibits a low resistance, the potential at the positive signal input terminal of the comparator 17 slightly rises by the resistor division by the on-resistance of the analog switch connected to the charge capacitance and the humidity sensor 23 which occurs immediately after the start of measurement so that the charging time of the capacitance measured by the count means 19 is shorter than the theoretical time so that the detection output represents a higher relative humidity than the actual relative humidity. This leads to a precision problem of the apparatus.

In the present embodiment, in the condition (high humidity range) in which the humidity sensor 23 exhibits a low resistance, a value corresponding to the first measurement time is set to the count means such as the count-down counter before the next measurement in order to compensate the first measured time, and the two count means are started simultaneously so that the offset count time is applied to the count-down counter. Further, in order to reduce the cost of the apparatus, the offset voltage corresponding to the first measurement time is applied to the reference voltage applied to the negative signal input terminal of the comparator instead of applying the offset count to the count means. Further, in order to reduce the environment measurement time, the compensation time determined by the predetermined operation by the control means such as the central processing unit is applied to the first measurement time to solve the offset of the potential of the positive signal input terminal of the comparator.

In accordance with the present invention, the measurable range of environment is expanded, the cost is reduced and the high performance and the high accuracy are attained.

Further, the affect by the stray capacity is reduced, the performance is maintained over the extended period and the offset is eliminated.

What is claimed is:

1. An environment measuring apparatus comprising:

a device having a resistance thereof varied with a change of environment;

a resistor connected to said device;

rectangular wave generation means for supplying a rectangular wave of a predetermined frequency across said device and said resistor; and measuring means for detecting a voltage between said device and said resistor to measure an environment level, wherein said rectangular wave generation means selectively supplies a rectangular wave of a first frequency and a rectangular wave of a second frequency lower than said first frequency in accordance with a detection result by said measuring means.

2. An environment measuring apparatus according to claim 1 wherein said rectangular wave generation means supplies the rectangular wave of the second frequency when a resistance of said device is high.

3. An environment measuring apparatus according to claim 1 wherein said rectangular wave generation means supplies the rectangular wave of the second frequency when a stray capacity of a circuit including said device and said resistor affects.

4. An environment measuring apparatus according to claim 1 wherein said device changes a resistance thereof with a change of humidity.

5. An environment measuring apparatus according to claim 1 wherein said rectangular wave generation means includes means for generating the rectangular wave of the first frequency and means for generating the rectangular wave of the second frequency.

6. An environment measuring apparatus according to claim 1 wherein said resistor is of low resistance when said device assumes a low resistance, and of high resistance when said device assumes a high resistance.

7. An environment measuring apparatus according to claim 6 wherein said resistor includes a resistor of a low resistance and a resistor of a high resistance.

8. An environment measuring apparatus according to claim 1 wherein said measuring means further includes control means for controlling an image forming apparatus in accordance with a result of measurement of said measuring means.

* * * * *

UNITED STATES PATENT AND TRADEMARK OFFICE
CERTIFICATE OF CORRECTION

PATENT NO. : 5,585,559
DATED : December 17, 1996
INVENTOR(S) : Shigeo HATA

It is certified that error appears in the above-indentified patent and that said Letters Patent is hereby corrected as shown below:

COLUMN 7

Line 8, "he" should read --the--.

COLUMN 13

Line 34, "t=CRln(Vin/(Vin-Vref)     (2)" should read --t=CRln(Vin/(Vin-Vref))     (2)--.

COLUMN 14

Line 56, "t-t'=C(Rln((R+Rz)/R-YRzln(R/(R+Rz)))" should read --t-t'=C(Rln((R+Rz)/R-YRzln(R/(R+Rz))))--

UNITED STATES PATENT AND TRADEMARK OFFICE
CERTIFICATE OF CORRECTION

PATENT NO. : 5,585,559
DATED : December 17, 1996
INVENTOR(S) : Shigeo HATA

It is certified that error appears in the above-indentified patent and that said Letters Patent is hereby corrected as shown below:

COLUMN 16

Line 13, "including" should read --includes--;

Line 14, "affects" should read --effects--.

Signed and Sealed this

Fifteenth Day of July, 1997

Attest:

BRUCE LEHMAN

Attesting Officer

Commissioner of Patents and Trademarks